(12) United States Patent
Chiou et al.

(10) Patent No.: US 11,045,435 B2
(45) Date of Patent: Jun. 29, 2021

(54) METHODS FOR TREATING OCULAR DISEASES

(71) Applicant: NATUREWISE BIOTECH & MEDICALS CORPORATION, Taipei (TW)

(72) Inventors: George Chung-Yih Chiou, Taipei (TW); Chia-Nan Chen, Taipei (TW)

(73) Assignee: NATUREWISE BIOTECH & MEDICALS CORPORATION, Taipei (TW)

( * ) Notice: Subject to any disclaimer, the term of this patent is extended or adjusted under 35 U.S.C. 154(b) by 0 days.

(21) Appl. No.: 15/720,785

(22) Filed: Sep. 29, 2017

(65) Prior Publication Data

US 2018/0085329 A1   Mar. 29, 2018

Related U.S. Application Data

(60) Provisional application No. 62/401,725, filed on Sep. 29, 2016.

(51) Int. Cl.
| | | |
|---|---|---|
| *A61K 31/185* | (2006.01) | |
| *A61K 9/00* | (2006.01) | |
| *A61K 31/16* | (2006.01) | |

(52) U.S. Cl.
CPC ......... *A61K 31/185* (2013.01); *A61K 9/0014* (2013.01); *A61K 9/0048* (2013.01); *A61K 9/0053* (2013.01); *A61K 31/16* (2013.01)

(58) Field of Classification Search
CPC .. A61K 31/185; A61K 9/0014; A61K 9/0048; A61K 9/0053; A61K 31/16
See application file for complete search history.

(56) References Cited

U.S. PATENT DOCUMENTS

| | | | | |
|---|---|---|---|---|
| 2005/0074497 A1* | 4/2005 | Schultz | ................ | A61K 9/0048 424/486 |
| 2010/0056522 A1 | 3/2010 | Yoneda et al. | | |
| 2010/0256401 A1* | 10/2010 | Huang | ................... | A61K 31/16 549/469 |

FOREIGN PATENT DOCUMENTS

| | | |
|---|---|---|
| CA | 2946086 A1 | 10/2015 |
| JP | 2011-20999 A | 2/2011 |
| JP | 2011-513382 A | 4/2011 |
| WO | WO 2008/123395 A1 | 10/2008 |
| WO | WO 2009/109900 A1 | 9/2009 |

OTHER PUBLICATIONS

Barakat and Kaiser, Expert Opin. Investig. Drugs (2009) 18(5):637-646 (Year: 2009).*
Good et al. British Journal of Ophthalmology 2011;95:1111-1114) (Year: 2011).*
Yang et al. PLOS One Nov. 1, 2013 vol. 8 Issue 11 e81592, pp. 1-12. (Year: 2013).*
Wedge et al. Cancer Research 62, 4645-4655, Aug. 15, 2002 ZD6474 Inhibits Vascular Endothelial Growth Factor Signaling, Angiogenesis, and Tumor Growth following Oral Administration (Year: 2002).*
Walpole et al. The weight of nations: an estimation of adult human biomass, BMC Public Health 2012 12:439. (Year: 2012).*
International Search Report and the Written Opinion of the International Searching Authority, dated Dec. 27, 2017 for International Application No. PCT/CN2017/104345.
Chan et al., "Attenuation of Choroidal Neovascularization by Histone Deacetylase Inhibitor," PLoS One, vol. 10, No. 3, dated Mar. 25, 2015, pp. 1-32.
Crosson et al., "Inhibition of Histone Deacetylase Protects the Retina from Ischemic Injury," Investigative Ophthalmology & Visual Science, vol. 51, No. 7, dated Jul. 2010, pp. 3639-3645.
Desjardins et al., "Histone Deacetylase Inhibition Restores Retinal Pigment Epithelium Function in Hyperglycemia," PLos One, vol. 11, No. 9, dated Sep. 12, 2016, pp. 1-16.
Fang et al., "Vorinostat Modulates the Imbalance of T Cell Subsets, Suppresses Macrophage Activity, and Ameliorates Experimental Autoimmune Uveoretinitis," Neuromolecular Med., vol. 18, No. 1, 2016 (published online Jan. 21, 2016), pp. 134-145.
Xiao et al., "Trichostatin A, a histone deacetylase inhibitor, suppresses proliferation and epithelial-mesenchymal transition in retinal pigment epithelium cells," Journal of Cellular and Molecular Medicine, vol. 18, No. 4, 2014, pp. 646-655.

* cited by examiner

*Primary Examiner* — Kortney L. Klinkel
*Assistant Examiner* — William Y Lee
(74) *Attorney, Agent, or Firm* — Birch, Stewart, Kolasch & Birch, LLP

(57) ABSTRACT

The present invention is related to a method for treating an ocular disease, particularly a diabetes related ocular disease, comprising administering to a subject in need thereof an effective amount of a group of compounds having a structure of Formula A1, wherein the ocular disease is selected from the group consisting of proliferative vitreoretinopathy (PVR), uveitis, glaucoma and age related macular degeneration (AMD), and the diabetes related ocular disease is selected from the group consisting of diabetic retinopathy (DR) and diabetic macular edema (DME).

6 Claims, 13 Drawing Sheets

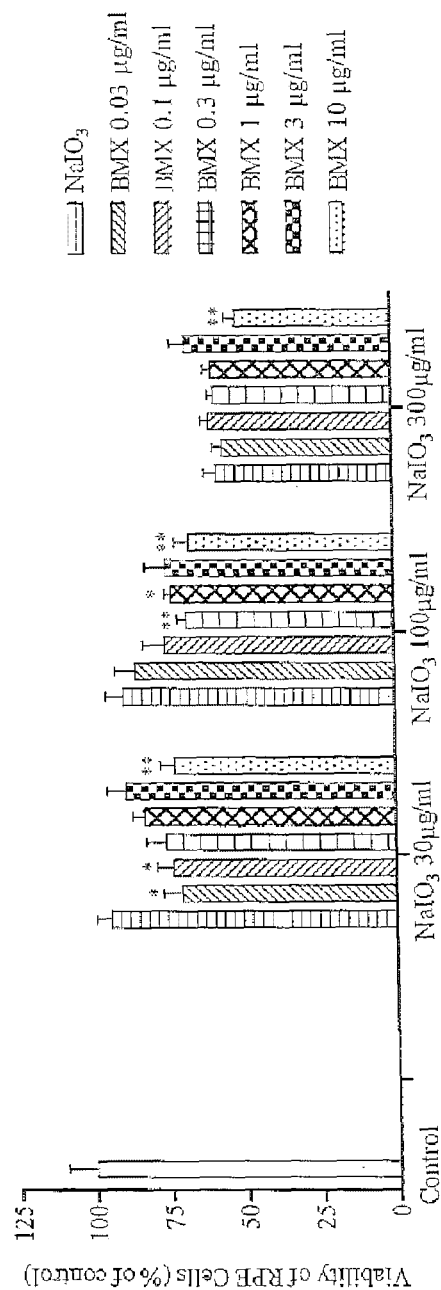
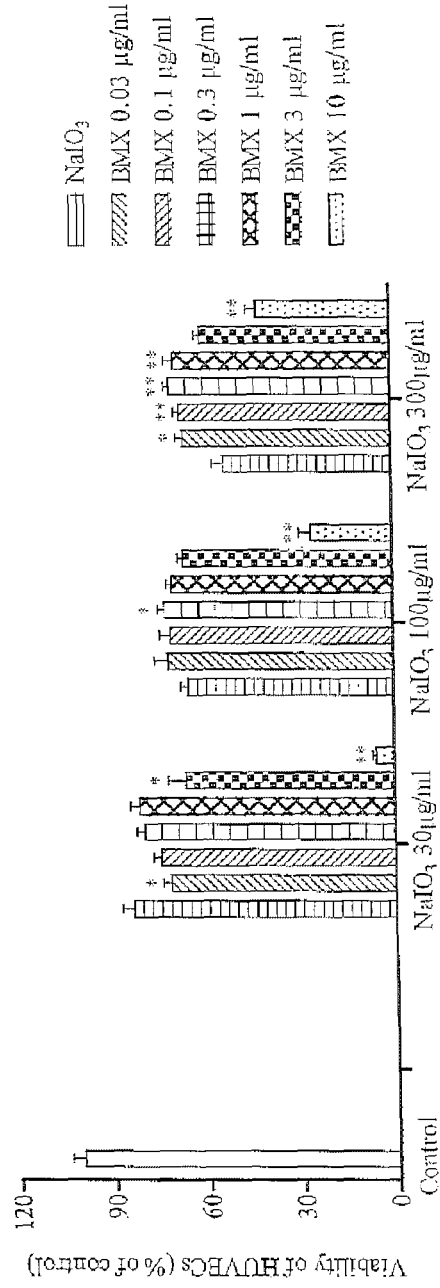
Fig. 3A
Fig. 3B

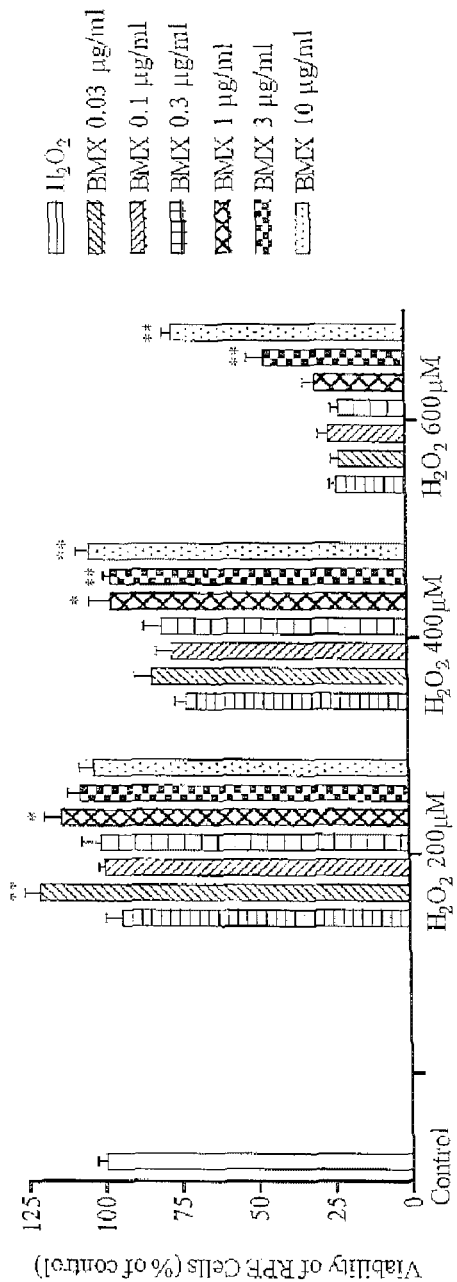
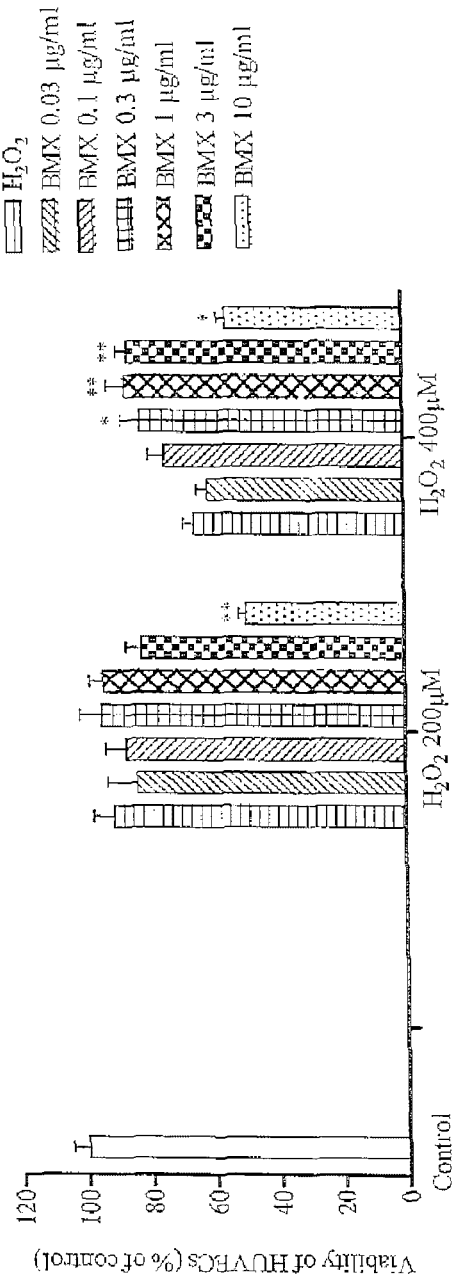
Fig. 4A
Fig. 4B

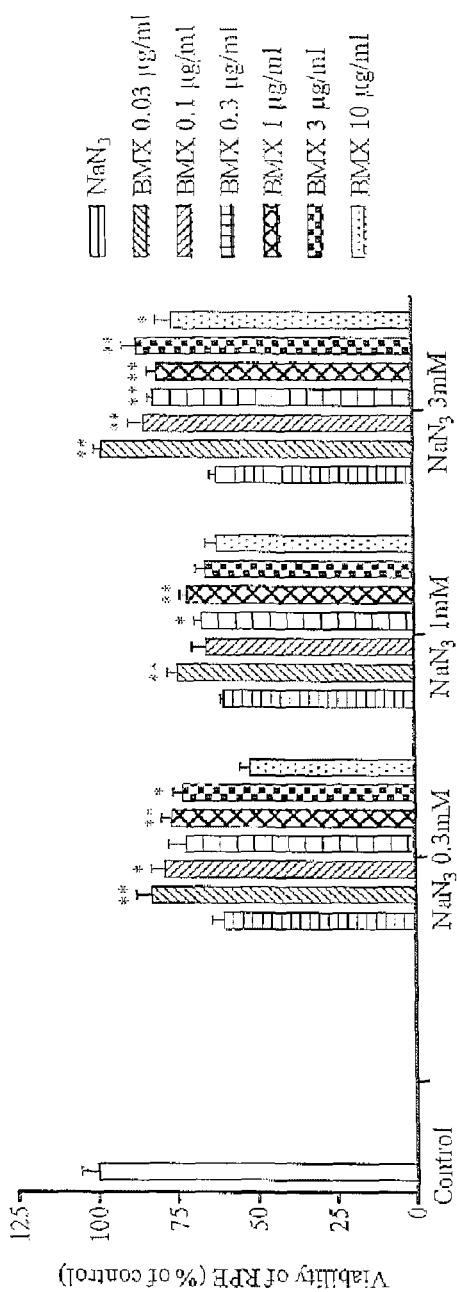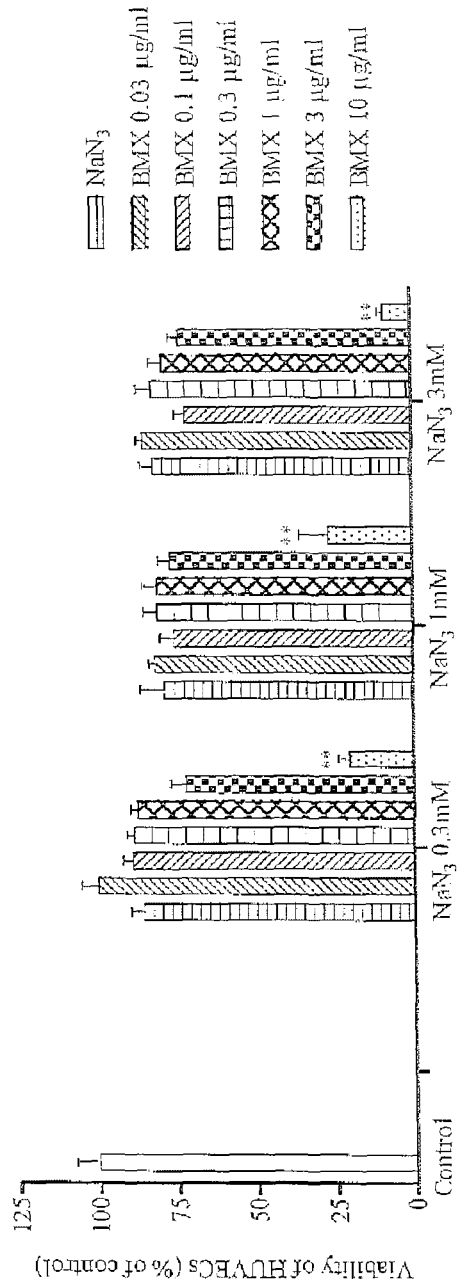
Fig. 5A
Fig. 5B

METHODS FOR TREATING OCULAR DISEASES

CROSS REFERENCE TO RELATED APPLICATIONS

This non-provisional application claims the benefit under 35 U.S.C. § 119(e) to U.S. Provisional Application No. 62/401,725, filed on Sep. 29, 2016, which is hereby expressly incorporated by reference into the present application.

FIELD OF THE INVENTION

The present invention pertains to a method for treating an ocular disease.

BACKGROUND OF THE INVENTION

The diabetic retinopathy (DR) and diabetic macular edema (DME) are the leading cause of adult blindness and the most common complication of diabetes. (Aiello L P et al. Diabetic retinopathy. Diabetes Care 21:143-156, 1998.) It affects more than 30% of people with diabetes, ultimately leading to retinal edema, neovascularization, and vision loss in many patients. Vascular change, including breakdown of the blood-retinal barrier (BRB), thickening of the capillary basement membrane, and reduction in the number of pericytes and increment in the number of acellular capillaries, have been widely documented in DR. (Yang L P et al. Baicalein reduces inflammatory process in a rodent model of diabetic retinopathy. Inv. Opthalmol. Vis. Sci 50:2319-2327, 2009.) Capillary cells are not the only retinal cells that undergo apoptotic death in diabetes. It was reported that a greater-than-normal frequency of neovascular cells became TUNEL (BrdU-Red DNA fragmentation)-positive in the retinas of humans and animals with diabetes. Although retinal vasculature is central to the development of diabetic retinopathy, there is accumulating evidence that neuroretinal functional is also compromised during the diseases, often before overt vessel changes. (Barbe A J et al. Neural apoptosis in the retina during experimental and human diabetes. Early onset and effect of insulin. J. Clin Invest. 102:783-791, 1998.)

For example, deficits in visual functioning, such as loss of color vision, contrast sensitivity, and abnormalities in the electroretinogram, have been documented in patients shortly after the diagnosis of diabetes and before the detection of clinically evident vascular retinopathy. (Phipps J A et al. Paired-fflash identification of rod and cone dysfunction in the diabetic rat. Inv Ophthalmol Vis Sci 45:4592-4600, 2004.) Early neuronal changes are also apparent in retinas of experimental rodent models of diabetes, including neurophysiological defects similar to those described in human diabetes. Because neuroretinal changes occur at an early stage of the disease process, it has been proposed that they may play a causative or contributory role in the initiation and progression of the vascular pathology associated with diabetic retinopathy. (Ward M M et al. Glutamate uptake in retinal glial cells during diabetes. Diabetologia 48:351-360, 2005.) In previous research studies, accumulating evidences confirmed the notion that inflammation in the retina, characterized by the activation of microglia and astroglia, is involved in the pathogenesis of DR. DR is a chronic, low-grade inflammatory disease. (Fan J W et al. Pharmacologic induction of heme oxygenase-1 plays a protective role in diabetic retinopathy in rats. Inv Ophthalmol Vis. Sci. 53:6541-6556, 2012.) Diabetic conditions lead to an elevation of pro-inflammatory cytokine expression within the retina, which activates microglial cells. In response to an activating stimulus, quiescent microglia undergoes a series of stereotyped morphologic, phenotypical, and functional changes. Activated microglia thereby stimulates a cycle of inflammation that recruits leukocytes, causes vascular breakdown, and directly induces glial dysfunction and neuronal cell death through the release of cytotoxic substances. (Steinle J J et al. Intra-ophthalmic artery chemotherapy triggers vascular toxicity through endothelial cell inflammation and leukosasis. Inv Ophthalmol Vis Sci 53: 2439-2445, 2012.) Miller cells are the principal glia of the retina. They span the entire thickness of the retina from the inner limiting membrane to the photoreceptor layer, and the processes make contact with most neural cells. (Bringmann A & Wiedemann P. Müller glial cells in retinal disease. Ophthalmologica 227:1-19, 2012.) They also form end feet on both large vessels and capillaries in the inner and outer retinal vessels beds. (Distler C and Dreher Z. Glia cells of the monkey retian-II. Müller cells. Vision Res 36:2381-2394, 2012.) Müller glia is vital for maintaining normal neuronal and vascular function in the retina. Several studies over the past two decades have provided evidence that Miller glia is adversely affected early in the course of diabetes. Miller glia in both humans and experimental diabetes acquires a reactive phenotype characterized by cellular hyperplasia and up-regulation of glial fibrillary acidic protein (GFAP). (Yong, P H et al. Evidence supporting a role for N'-(d-formyl-3,4-dehydropiperidino) lysine accumulation in Miller glia dysfunction and death in diabetic retinopathy. Molecular Vision 16:2524-2538, 2010.) In diabetic animals, these biotic changes are accompanied by several dysfunctional responses, including alterations in their capacity to regulate potassium and glutamate in the extracellular space, accumulation of γ-aminobutyric acid, up-regulation of pro-inflammatory cytokines, and increased expression of angiogenic growth factors, such as vascular endothelial growth factor (VEGF). (Ferrara N. Vascular endothelial growth factor. ArteriosclerThromb Vase Biol. 29:789-791, 2009)

However, it is still desirable to find some new approach to treat an ocular disease.

BRIEF SUMMARY OF THE INVENTION

It was unexpectedly found in the present invention that some new compounds are potent anti-oxidants and ocular blood flow facilitators, which are effective to prevent the breakdown of blood eye barrier induced by diabetic macular edema and production of VGEF and GFAP due to diabetic retinopathy. The unexpected discovery leads these compounds as potent drugs for the treatment of an ocular disease, particularly age-related macular degeneration (AMD) and diabetes related ocular disease, such as diabetic retinopathy (DR), diabetic macular edema (DME) or glaucoma.

Accordingly, in one aspect, the present invention features a method for treating an ocular disease, comprising administering to a subject in need thereof an effective amount of a compound having a structure of Formula A1:

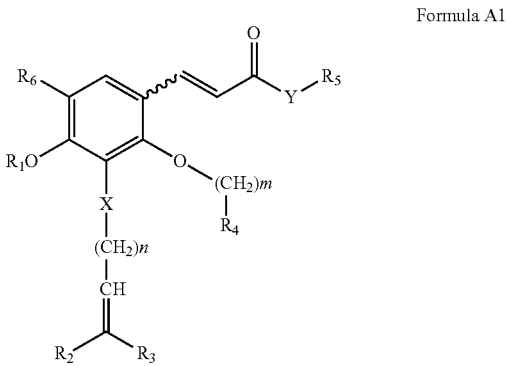

Formula A1 wherein
$R^1$ is hydrogen, alkyl, alkenyl, $C_5$-$C_6$ cycloalkyl, 5-membered or 6-membered unsaturated carbocycle or 5-membered or 6-membered heterocycle, or $(CH_2)mR^4$
X is C, —O—, —N— or —S—;
Y is —O—, —NH or —O—$C_1$-$C_4$ alkyl;
n is an integer of 0 to 10;
m is an integer of 0 to 5;
$R^2$ and R is independently $C_1$-$C_6$ alkyl;
$R^4$ is $C_5$-$C_6$ cycloalkyl or 5-membered or 6-membered unsaturated carbocycle or heterocycle which may be substituted with halogen, —$CF_3$, —$OR^7$ or —$NR^7R^8$, wherein $R^7$ and $R^8$ are independently hydrogen or $C_1$-$C_6$ alkyl;
$R^5$ is OH, $NH_2$ or $C_5$-$C_6$ cycloalkyl, 5-membered or 6-membered unsaturated carbocycle or heterocycle wherein the cycloalkyl, carbocycle and heterocycle may be optionally substituted with halogen, $NH_2$, $NO_2$, $C_1$-$C_6$ alkoxy, $C_{1-6}$ alkylthio, $OR^{7"}$, $NR^7R^8$ or $CF_3$; and
$R^6$ is H, $C_1$-$C_{10}$ alkyl which may be substituted by hydroxy or $C_2$-$C_{10}$ alkenyl, or together with $R_1$ being —$C_2H_2$—;
or a pharmaceutically acceptable salt, stereoisomer, enantiomer, prodrug or solvate thereof.

In another aspect, the present invention provides the use of a compound having a structure of Formula 1A for manufacturing a medicament in the treatment of an ocular disease, particularly a diabetes related ocular disease.

In one further aspect, the present invention provides a pharmaceutical composition for use in treating an ocular disease, particularly a diabetes related ocular disease, comprising the compound having a structure of Formula A1 and a pharmaceutically acceptable carrier.

In one embodiment of the invention, the ocular disease is proliferative vitreoretinopathy (PVR), uveitis, glaucoma or age related macular degeneration (AMD).

In one particular embodiment of the invention, the diabetes related ocular disease is diabetic retinopathy (DR) or diabetic macular edema (DME).

It is to be understood that both the foregoing general description and the following detailed description are exemplary and explanatory only and are not restrictive of the invention.

BRIEF DESCRIPTION OF THE DRAWINGS

FIG. 3A shows the effect of BMX on $NaIO_3$-induced injury in ARPE-19 cells. ARPE-19 cells were incubated with BMX and $NaIO_3$ for 72 h.

FIG. 3B shows the effect of BMX on $NaIO_3$-induced injury in HUVECs. HUVECs were incubated with BMX and $NaIO_3$ for 72 h. Data were expressed as means±SEM, n=6 in each group; *, P<0.05 and **, P<0.01 vs. $NaIO_3$ group.

FIG. 4A shows the effect of BMX on $H_2O_2$-induced injury in ARPE-19 cells. ARPE-19 cells were incubated with BMX and $H_2O_2$ for 24 h.

FIG. 4B shows the effect of BMX on $H_2O_2$-induced injury in HUVECs. HUVECs were incubated with BMX and $H_2O_2$ for 24 h. Data were expressed as means±SEM, n=6 in each group; *, P<0.05 and **, P<0.01 vs. $H_2O_2$ group.

FIG. 5A shows the effect of BMX on $NaN_3$-induced injury in ARPE-19 cells. ARPE-19 cells were incubated with BMX and $NaN_3$ for 72 h.

FIG. 5B shows the effect of BMX on $NaN_3$-induced injury in HUVECs. HUVECs were incubated with BMX and $NaN_3$ 72 h. Data were expressed as means±SEM, n=6 in each group; *, P<0.05 and **, P<0.01 vs. $NaN_3$ group.

DETAILED DESCRIPTION OF THE INVENTION

Figure 1A:
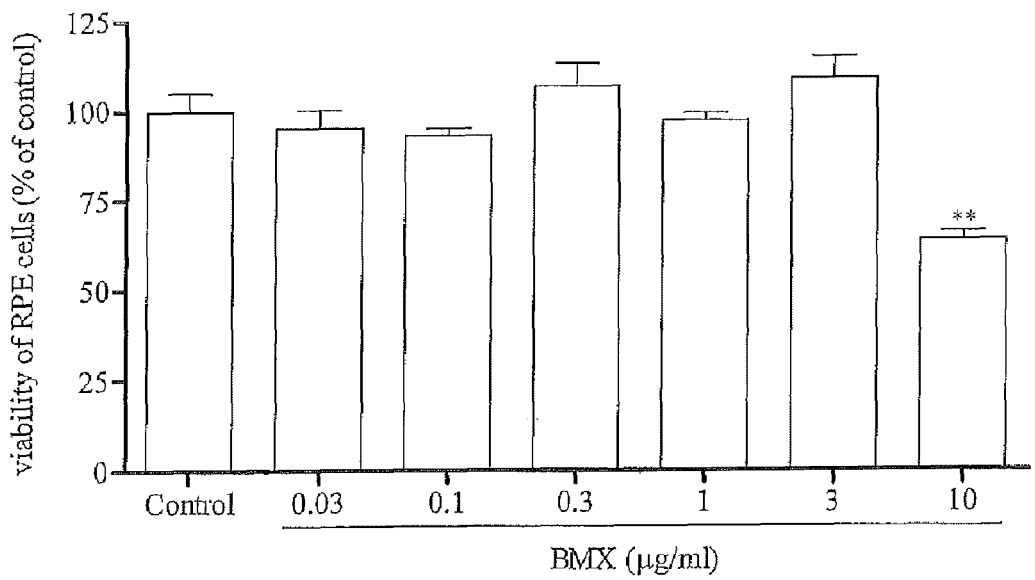
FIG. 1A shows the effect of COMPOUND I (hereinafter called as "BMX") on proliferation of ARPE-19 cells. ARPE-19 cells were incubated with BMX for 72 h.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

According to the invention, a new method for treating an ocular disease is provided. The compounds used in the invention are disclosed in U.S. Pat. No. 7,994,357, the content of which is hereby incorporated by reference in its entirety. The compound has a structure of Formula A1:

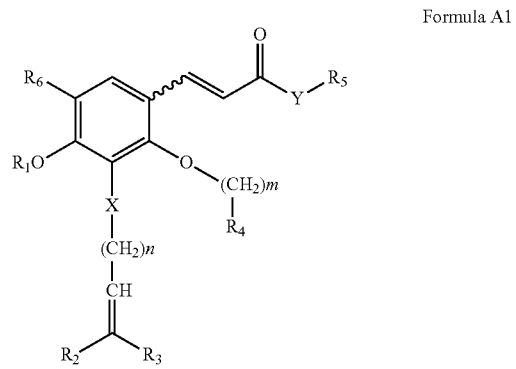

Formula A1 wherein
$R^1$ is hydrogen, alkyl, alkenyl, $C_5$-$C_6$ cycloalkyl, 5-membered or 6-membered unsaturated carbocycle or 5-membered or 6-membered heterocycle; $(CH_2)m$ $R^4$
X is C, —O—, —N— or —S—:
Y is —O—, —NH or —O—$C_1$-$C_4$ alkyl;
n is an integer of 0 to 10;
m is an integer of 0 to 5;
$R^2$ and $R^3$ is independently $C_1$-$C_6$ alkyl;
$R^4$ is $C_5$-$C_6$ cycloalkyl or 5-membered or 6-membered unsaturated carbocycle or heterocycle which may be substituted with halogen, —$CF_3$, —$OR^7$ or —$NR^7R^8$, wherein $R^7$ and $R^8$ are independently hydrogen or $C_1$-$C_6$ alkyl;
$R^5$ is OH, $NH_2$ or $C_5$-$C_6$ cycloalkyl, 5-membered or 6-membered unsaturated carbocycle or heterocycle wherein the cycloalkyl, carbocycle and heterocycle may be optionally substituted with halogen, $NH_2$, $NO_2$, $C_1$-$C_6$ alkoxy, $C_{1-6}$ alkylthio, $OR^7$, $NR^7R^8$ or $CF_3$; and
$R^6$ is H, $C_1$-$C_{10}$ alkyl which may be substituted by hydroxy or $C_2$-$C_{10}$ alkenyl, or together with $R_1$ being —$C_2H_2$—.

In one particular embodiment of the present invention, the compound is COMPOUND I (also called as "BMX"), that was derived from the semi-synthesis of osthole and play a novel role in learning and memory as reported in Yang Y C et al. (Yang Y C et al. Evid. Based Complement Alternat. Med. 2013: Article ID. 514908 (18 pages), 2013.):

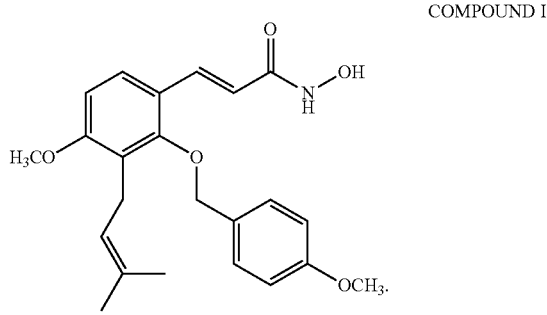 [SMILES: COc1ccc(COc2c(/C=C/C(=O)NO)ccc(OC)c2CC=C(C)C)cc1]

COMPOUND I

The term "ocular disease" as used herein refers to a disease or disorder associated with reduced ocular blood flow, including but not limited to proliferative vitreoretinopathy (PVR), uveitis, glaucoma and age related macular degeneration (AMD).

The term "diabetes related ocular disease" as used herein refers to a disease or disorder that is associated with, caused by or result from diabetes, including but not limited to diabetic retinopathy (DR), and diabetic macular edema (DME), which may be associated with oxidative stress and/or hypoxia-induced damages to the eyes, or more particularly to the retinal pigment epithelium (RPE).

The term "effective amount" as used herein refers to a sufficient amount of a compound of a general Formula A to provide desired therapeutic effects, or the induction of a particular type of response. The effective amount required varies from subject to subject, depending on the disease state, physical conditions, age, sex, species and weight of the subject, etc. However, an appropriate effective amount can be determined by one of ordinary skill in the art using only routine experimentation. For example, the compound of general Formula A1 may be administered orally to a subject 1-3 times a day. For each oral administration, the amount of the compound of general Formula A1 may be 0.5 to 50 mg, preferably 2-25 mg. The compound of general Formula A1 may also be administered to a subject through ophthalmological administration, 1-10 times daily. For example, one may use one drop of a preparation comprising the compound of general Formula A1 each time, 3 times daily. For topical ophthalmological administrations, 0.01-10% compound of general Formula A1 may be used, preferably, 0.1-1.0% compound of general Formula A1 may be used.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol, propylene glycol, cremophor, nanoparticles, liposome, polymer, and combinations thereof.

The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for topical administration include cream, ointment, gel, suspension, drops, emulsions, skin patches.

In addition to standard carriers, an oral pharmaceutical composition of the present invention may be supplemented with one or more excipients that are normally employed in oral formulations, such as surfactants, inhalants, solubilizers, stabilizers, emulsifiers, thickeners, coloring agents, sweetening agents, flavoring agents, and preservatives. Such excipients are well known to those skilled in the art.

According to the invention, the pharmaceutical composition may be administered to a subject through any route, such as oral administration, parenteral injection, eye injection (e.g., intravitreal injection), skin patch, or topical administration on eyes. The pharmaceutical compositions for topical administration on eyes may be formulated in the form of eye ointment, eye gel, eye cream, or eye drop.

The present invention is further illustrated by the following examples, which are provided for the purpose of demonstration rather than limitation.

EXAMPLES

Example 1: Effect on Oxidation

The mechanisms of the dysfunction or cell death of RPE may involve various factors, such as oxidative injury, degenerative changes in Bruch's membrane and damage to the choroidal vasculature. Different types of oxidative stress results in different patterns of oxidative damage to proteins in RPE cells and different patterns of loss of viability.

The retinal pigment epithelium (RPE) is a monolayer cell located between the retinal photoreceptors and the choroidal blood vessels, which plays a key role in the mechanical and metabolic support of the photoreceptors. In addition, RPE cell is the main element of some ocular diseases, such as proliferative vitreoretinopathy (PVR), uveitis and age related macular degeneration (AMD). AMD and other diseases, such as diabetic retinopathy (DR), are probably linked to the effects of oxygen radicals derived from light or metabolic reactions. Since the epithelium is very vulnerable to changes in oxygen tensions and oxygen radical-linked stress, reactive oxygen species (ROS) produced in the RPE during ischemia-linked diseases may be injurious to RPE cells. An important "early" event of AMD is the loss of RPE cells due to oxidative damage. Oxidative stress has been recognized to be involved in the etiology of several age-related chronic diseases, such as cancer, diabetes, neurodegenerative and cardiovascular diseases.

1.1 Materials

Thiazolyl blue tetrazolium bromide (MTT, purity>97.5%), Dulbecco's phosphate buffered saline (DPBS), hydrogen peroxide ($H_2O_2$, 50 wt. % solution in water), tert-butyl hydroperoxide (t-BHP, 70 wt. % in water), sodium iodate ($NaIO_3$, purity>99.5%), sodium azide ($NaN_3$, purity>99.5%) and Dulbecco's modified Eagle's medium/Ham's F12 (DMEM/F12, 1:1) were all purchased from Sigma-Aldrich Chemical Co. (St. Louis, Mo., USA). Human retinal pigment epithelium (ARPE-19) cells, human umbilical vein endothelial cells (HUVECs), fetal bovine serum (FBS), vascular cell basal medium and endothelial cell growth kit were purchased from ATCC (Manassas, Va., USA).

1.2 Cell Culture

ARPE-19 cells were grown in DMEM/F12 medium supplemented with 10% FBS, 100 units/ml penicillin G, and 100 µg/ml streptomycin sulfate. HUVECs were grown in vascular cell basal medium supplemented with endothelial cell growth kit. Cells were incubated in a humidified incubator at 37° C. under 5% $CO_2$ and 95% air.

1.3 Effect of BMX on the Viability of ARPE-19 Cells and HUVECs

MTT assay was used to measure the viability of ARPE-19 cells and HUVECs. $2\times10^5$ ARPE-19 cells or $5\times10^4$ HUVECs were seeded in 96-well plates (100 l/well) and allowed to grow overnight. Negative control was prepared by adding 100 μl medium without cells. The cells were then treated with fresh medium with COMPOUND I (0.03, 0.1, 0.3, 1, 3 and 10 μg/ml) and/or oxidants ($NaIO_3$, $H_2O_2$, t-BHP and $NaN_3$) for 12, 24, or 72 hours (200 μl/well). The vehicle control group was treated with vehicle. 20 μl MTT (5 mg/ml) was added to wells, and incubated for another 4 h. After incubation, the medium was discarded and 100 μl DMSO was added to solubilize formazan produced from MTT by the viable cells. Absorbance was measured at 570 nm using a microplate reader (Bio-Rad Laboratories, Inc., CA). Cells viability was calculated according to the following formula: Viability of cells (%)=(absorbance in tested sample−absorbance in negative control)/(absorbance in vehicle control−absorbance in negative control)×100%.

1.4 Hypoxia Treatment

Cells were allowed to attach overnight, and then exposed to COMPOUND I or vehicle under hypoxic condition for 72 h. Hypoxic conditions (1% $O_2$, 5% $CO_2$ and 94% $N_2$) were maintained by using a temperature and humidity controlled environmental C-chamber by $O_2$ and $CO_2$ controllers (Proox Model 110 and Pro $CO_2$ model 120, Biospherix Ltd., Redfield, N.Y., USA) with $N_2$ and $CO_2$ gas sources.

1.5 Statistical Analysis

All data were expressed as means±S.E.M. Statistical analysis was performed using the Student's t-test. A value of $P<0.05$ was considered to be statistically significant.

1.6 Results 1.6.1 Cytotoxicity of Compound I in ARPE-19 Cells and HUVECs

Figure 1B:
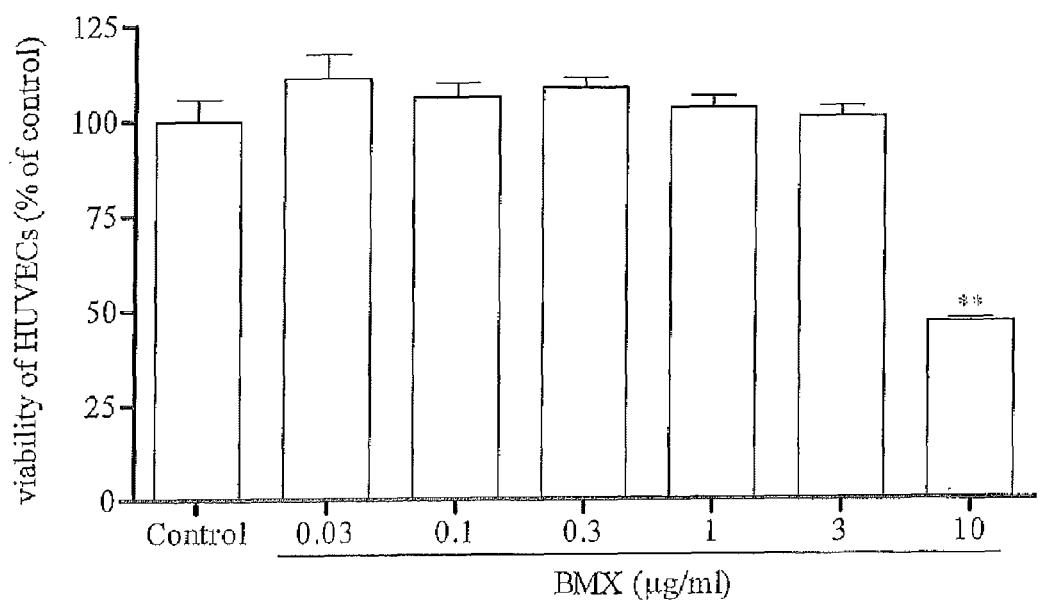
FIG. 1B shows the effect of BMX on proliferation of HUVECs. HUVECs were incubated with BMX for 72 h. Data were expressed as means±SEM with n=6 in each group. ** P<0.01 BMX group vs. vehicle control group.

The results showed that BMX did not affect cell growth in ARPE-19 cells and HUVECs from 0.03 μg/ml to 1 μg/ml. However, COMPOUND I significantly inhibited the proliferation of ARPE-19 cells and HUVECs at the concentration of 10 μg/ml by 36% and 47%, respectively ($P<0.01$, FIG. 1A and FIG. 1B).

Figure 2A:
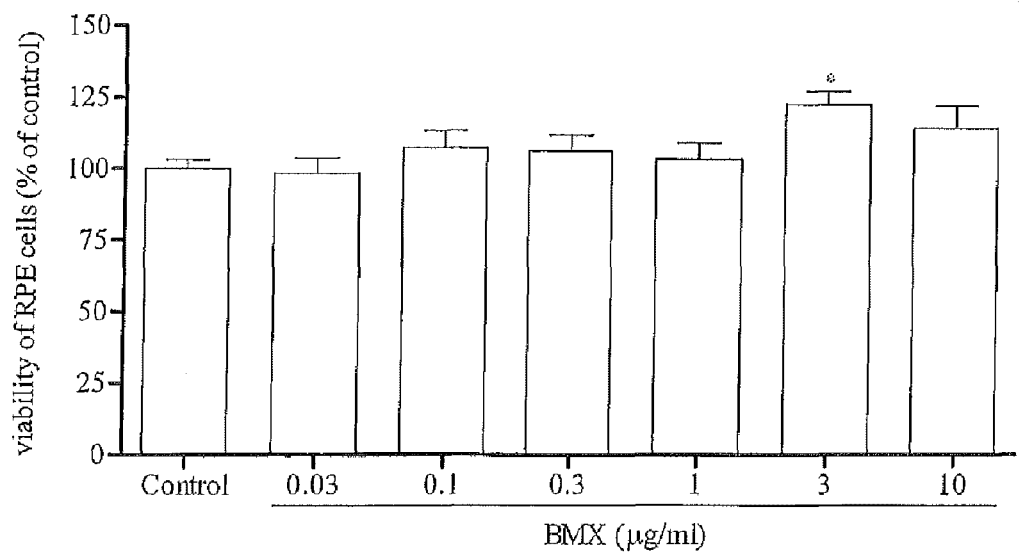
FIG. 2A shows the effect of BMX on hypoxia-induced injury in ARPE-19 cells. ARPE-19 cells were incubated with BMX for 72 h.
Figure 2B:
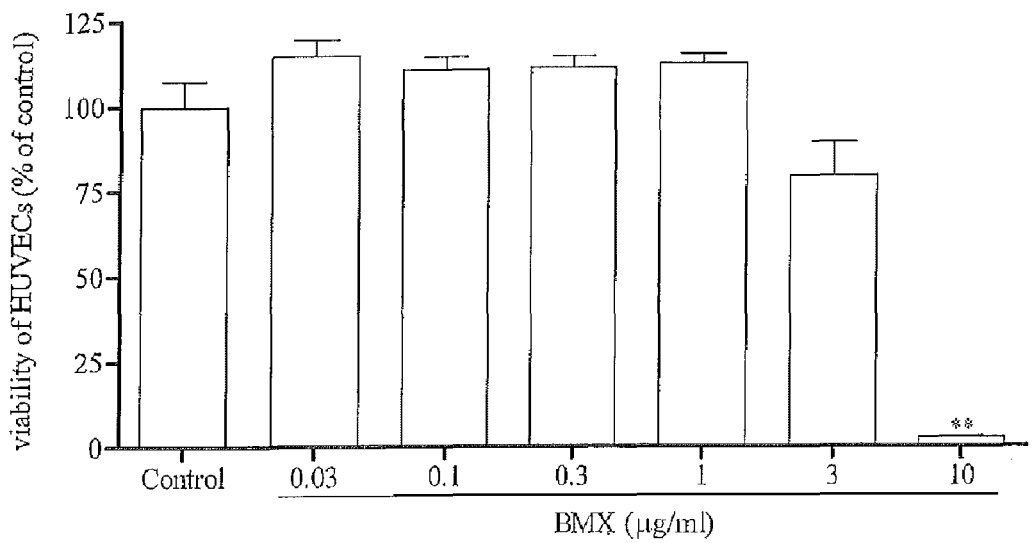
FIG. 2B shows the effect of BMX on hypoxia-induced injury in HUVECs. HUVECs were incubated with BMX for 72 h. Control group was treated with vehicle under hypoxic condition (1% $O_2$. 5% $CO_2$ and 94% $N_2$) for 72 hours. Data were expressed as means±SEM, n=6 in each group: *, P<0.05 and **, P<0.01 vs. control group.

1.6.2 Effect of Compound I on Hypoxia-Induced Damage in ARPE-19 Cells and HUVECs Except at 3 μg/ml, COMPOUND I (BMX) increased the viability of ARPE-19 cells by 22%, COMPOUND I had no effect on ARPE-19 cells in hypoxic condition from 0.03 μg/ml to 10 μg/ml ($P<0.05$, FIG. 2A). At the concentration of 10 μg/ml, COMPOUND I significantly decreased the viability of HUVECs in hypoxic condition by 98% ($P<0.01$, FIG. 2B).

1.6.3 Effect of Compound I on $NaIO_3$-induced Injury in ARPE-19 Cells and HUVECs At the concentration of 10 μg/ml, COMPOUND I significantly enhanced the viability of $NaIO_3$-induced injury in both ARPE-19 cells and HUVECs ($P<0.01$, FIG. 3A and FIG. 3B). However, COMPOUND I reversed 300 μg/ml $NaIO_3$-induced injury in HUVECs from 0.03 μg/ml to 1 μg/ml ($P<0.01$, FIG. 3B).

1.6.4 Effect of Compound I on $H_2O_2$-Induced Injury in ARPE-19 Cells and HUVECs At the concentration of 3 μg/ml and 10 μg/ml, COMPOUND I reversed 400, M and 600 μM $H_2O_2$-induced injuries in ARPE-19 cells ($P<0.01$, FIG. 4A). However, 10 μg/ml COMPOUND I enhanced 200 μM and 400 μM $H_2O_2$-induced injuries by 41% and 10% in HUVECs, respectively (FIG. 4B).

1.6.5 Effect of COMPOUND I on $NaN_3$-Induced Injury in ARPE-19 Cells and HUVECs COMPOUND I significantly reversed $NaN_3$-induced injury in ARPE-19 cells (FIG. 5A). From 0.03 μg/ml. COMPOUND I didn't affect $NaN_3$-induced injury in HUVECs, however. 10 g/ml COMPOUND I enhanced 0.3, 1 and 3 mM $NaN_3$-induced injury by 65%, 52% and 72% in HUVECs, respectively ($P<0.01$, FIG. 5B).

1.6. 6 Effect of Compound I on t-BHP-Induced Injury in ARPE-19 Cells and HUVECs

Figure 6A:
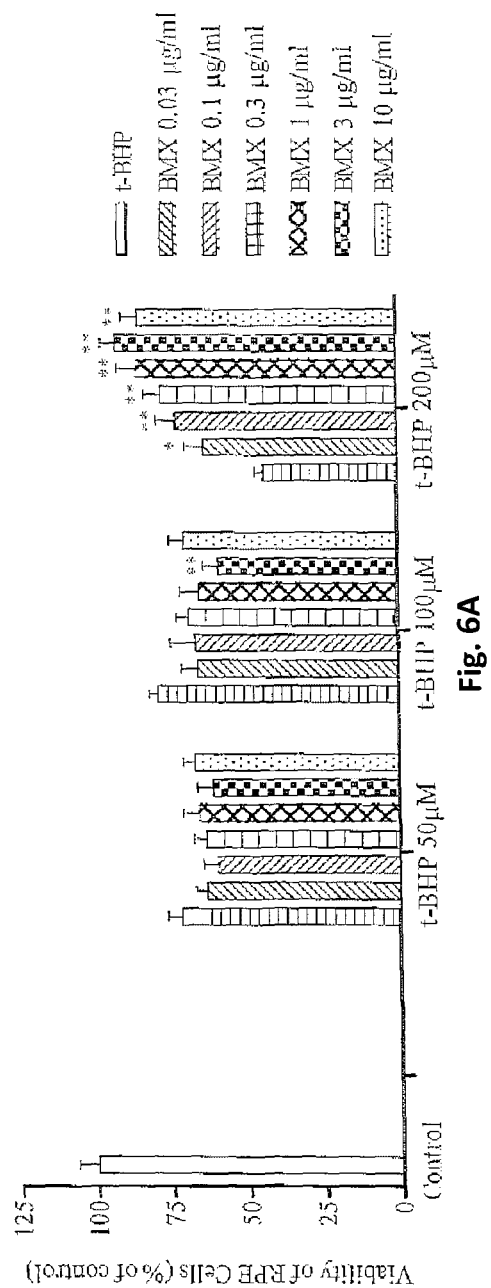
FIG. 6A shows the effect of BMX on t-BHP-induced injury in ARPE-19 cells. ARPE-19 cells were incubated with BMX and t-BHP for 12 h.
Figure 6B:
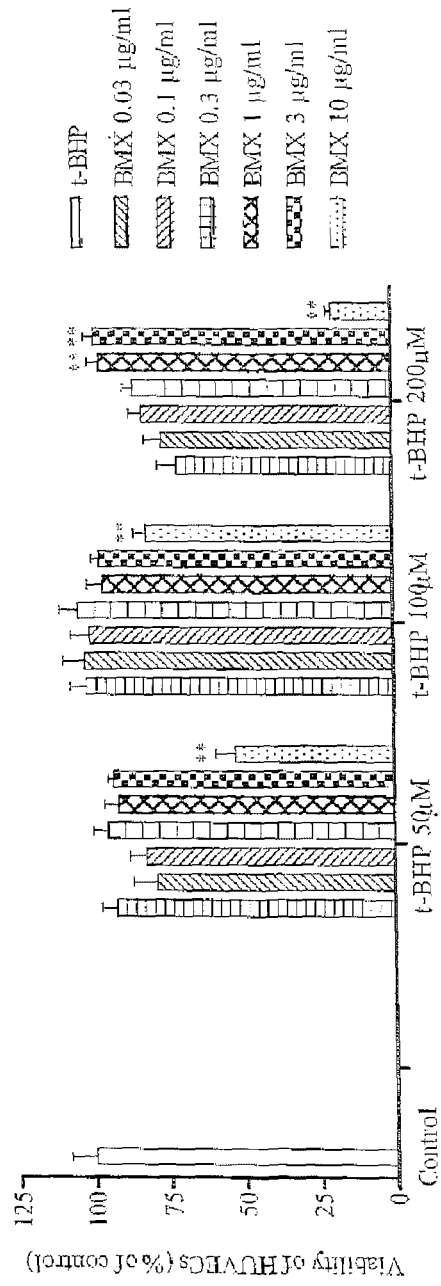
FIG. 6B shows the effect of BMX on t-BHP-induced injury in HUVECs. HUVECs were incubated with BMX and t-BHP for 12 h. Data were expressed as means±SEM, n=6 in each group; *, P<0.05 and **, P<0.01 vs. t-BHP group.

From 0.03 μg/ml to 10 g/ml, COMPOUND I reversed 200 μM t-BHP-induced injury in ARPE-19 cells (FIG. 6A). At the concentration of 1 μg/ml and 3 μg/ml, COMPOUND I reversed 200 I-M t-BHP-induced injury in HUVECs by 26% and 28%, respectively ($P<0.01$, FIG. 6A). However, 10 μg/ml COMPOUND I enhanced 50, 100 and 200 μM t-BHP-induced injury in HUVECs by 40%, 20% and 51%, respectively ($P<0.01$, FIG. 6B).

It was concluded that BMX reversed oxidative injuries of RPE cells caused by all oxidants, including hypoxia, $H_2O_2$, $NaN_3$ and t-BHP except $NaIO_3$, which was enhanced by BMX. On the contrary, BMX at high concentration (10 μg/ml) enhanced oxidative injuries induced by all, including hypoxia, $H_2O_2$, $NaN_3$ and t-BHP except $NaIO_3$ on HUVEC. The lower concentrations of BMX either showed no effect or slight reverse of oxidative injuries induced by all oxidants, including $NaIO_3$ on the HUVEC cells. These results indicate that BMX is a potent antioxidant on all oxidants except $NaIO_3$ on RPE cells. On the contrary, it is less efficacious or non-effective to reverse the injuries induced by oxidants and even enhanced the oxidative injuries at high concentration (10 μg/ml) on HUVECs.

In summary, BMX is a potent antioxidant to ocular RPE cells but not to non-ocular specific HUVEC cells, indicating BMX is an excellent agent to be used to treat eye related diseases such as diabetic retinopathy and diabetic macular edema.

Example 2: Enhancement of Ocular Blood Flow (OBF)

Improvement of ocular blood flow is essential in diabetic retinopathy, diabetic macular edema, glaucoma and ischemic eye diseases because the supply of most needed nutrients and oxygen can be maintained at normal or close to normal levels as a result. Although the blood flow of coronary is quite high at 2-8 ml/min/g tissue, the blood flow of choroid is even higher at 13 ml/min/g tissue. Chronic reduction in ocular blood flow may result in deterioration of visual field and optic nerve head whereas acute ischemia for more than 45 minutes might cause irreversible blindness.

Ocular blood flow is closely related to numerous eye diseases, including glaucoma, ischemic retinopathy, diabetic retinopathy and age-related macular degeneration (AMD). Thus, maintenance of normal ocular blood flow is essential to prevent/treat the aforementioned eye diseases.

2.1 Materials 0.5% alcaine was purchased commercially. A 20% sterilized hypertonic saline solution was prepared in the laboratory. Colored microspheres were purchased from E-Z Trac (Los Angeles, Calif.). The colored microspheres were diluted with saline containing 0.01% (v/v) of Tween 80 to prevent the microspheres from sticking together. Two million microspheres in 0.4 ml were injected at each time point.

Female New Zealand white rabbits weighing 2-3.0 kg, were purchased commercially. Animal care and treatment were followed by the institutional guidelines.

2.2 Methods

Rabbits were anesthetized with 35 mg/kg ketamine and 5 mg/kg Balanzine (10% xylazine) by intramuscular injection. Half of the initial dose was given every one hour thereafter. The left ventricle was cannulated through the right carotid artery for injection of colored microspheres and the femoral artery was cannulated for collection of blood samples. The left eye was treated with one drop of proparacaine hydrochloride ophthalmic solution (Bausch & Lomb, Inc., Tampa, Fla., USA). The needle was inserted directly into the anterior chamber of the left eye, which was connected to the 40 mmHg saline manometer. The ocular hypertensive model reduced the ocular blood flow to approximately one third of the normal valued. 50 µl of 10 g/l COMPOUND I or vehicle (30% HP-β-CD solutions) was instilled topically to the left eye 30 minutes after the ocular hypertensive model was built. The ocular blood flow was measured by colored microspheres at 0, 30, 60 and 120 minutes after treatment with COMPOUND I or vehicle. At each time point, 2 million microspheres were injected as a reference, and blood samples were taken from the femoral artery for exactly one minute following injection of the microspheres. The blood sample was collected in a heparinized tube and the volume was recorded. The rabbits were euthanized with an injection of 100 mg/kg pentobarbital sodium after the last blood sampling. The left eyes were enucleated and dissected into the iris, ciliary body, retina and choroid. All the tissues were weighed.

The details of sample processing and microspheres counting were provided by E-Z Trac (Los Angeles, Calif., USA). In brief, the blood hemolysis reagent was added to the microfuge tubes with the blood sample, then vortexes and centrifuged for 30 minutes at 6000 rpm. The supernatant was removed, and then tissue/blood digest reagents I and II were added. The tubes were capped, vortexed, and centrifuged for 30 minutes. The supernatant was removed, and the counting reagent was added, vortexed, and centrifuged for 15 minutes. The supernatant was removed, and the microspheres were resuspended in a precise volume of the counting reagent. The number of microspheres was counted by the hemocytometer under the microscope. Tissue/blood digest reagent I was added to the microfuge tubes with the tissue samples, sealed, and heated at 95° C. for 15 minutes. Then the tubes were vortexed for 30 seconds, reheated, and revortexed until all tissue samples were dissolved. The tissue/blood digest reagent II was added while the tissue samples were still hot, then the tubes were capped, vortexed, and centrifuged for 30 minutes. The protocol thereafter was the same as that used to process the blood samples, and the microspheres were counted.

The blood flow of each tissue at a certain time point was calculated according to the following formula: Qm=(Cm× Qt)/Cr. Qm is the blood flow of a tissue in terms of 0.1l/min/mg, Cm is the microsphere numbering of tissue, Qr is the flow rate of blood sample in terms of µl/min, and Cr is the microsphere number in the referenced blood sample.

2.3 Results

Figure 7:
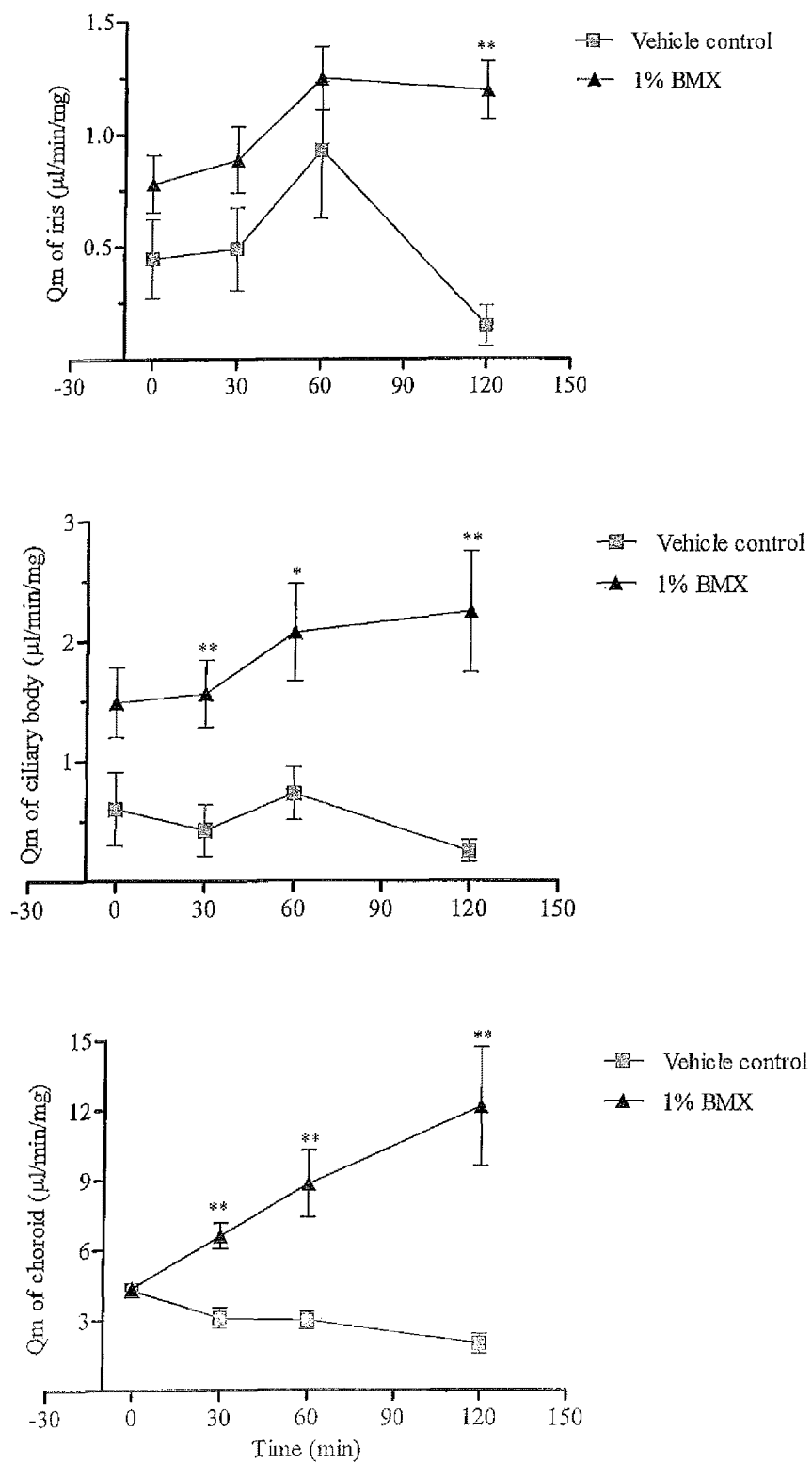
FIG. 7 shows the effect of 1% BMX on Ocular Blood Flow in Rabbit with Experimental Ocular Hypertension. Data were expressed as means±SEM, n=6 in each group; *, P<0.05 and **, P<0.05 vs control group.

The blood flow in all tissues was significantly increased by 1% COMPOUND I at 120 minutes after drug instillation (FIG. 7). However, the blood flow in ciliary body and choroid was also markedly increased at 30 minutes and 60 minutes after drug instillation (FIG. 7).

There are numerous eye diseases which are caused by the reduction of ocular blood flow; particularly in choroid, retina and iris. They include, but not limited to diabetic retinopathy, diabetic macular edema, glaucoma, age related macular degeneration, ischemic retinopathy and the like. Thus, enhancement of ocular blood flow is beneficial to DR and DME. This research showed a potent enhancement of ocular blood flow by BMX, indicating that it can be used to treat DR or DME efficaciously.

Example 3: Effect of Compound I on Blood-Retinal Barrier Breakdown in Streptozotocin-Induced Diabetic Macular Edema Diabetic macular edema (DME) is the most common cause of visual loss in persons over 50 years of age in the developed world. Diabetes mellitus, the cause of DME, through subclinical inflammation is increasing in incidence and prevalence worldwide, becoming epidemic not only in the developed world, but in the underdeveloped world as well. This complication occurs mainly because of DR, a vascular complication of diabetic that frequently is diagnosed and treated later than it should, when the conditions that impair vision already took place. DR destroys vision via retinal neovascularization and macular edema. The pathophysiology of DME involves dilated capillaries, retinal microaneurysms, and loss of pericytes, with eventual impairment of the blood-retinal barrier (BRB). Breakdown of the BRB results in fluid leakage into the extracellular space, which disrupts macular structure and function on a cellular level.

The interleukin-1 blocking compounds are effective in inhibiting IL-1 induced inflammation and are also effective in inhibiting ophthalmic wound healing. Given that various inflammatory mediators appear to play a role in promoting DME, we speculate that COMPOUND I with its anti-inflammatory properties, may exert the capacity to block diabetes-induced DME.

3.1 Materials and Methods

After a 16-hour fast, Sprague-Dawley female rats weighing 200-220 g received a single 60 mg/kg intraperitoneal injection of Streptozotocin (STZ; Sigma-Aldrich, St. Louis, Md.) in 10 mM sodium citrate buffer (pH 4.5; Sigma-Aldrich, St. Louis, Md.). Control rats were fasted and received the buffer alone. Rats with blood glucose levels higher than 375 mg/dL 7 days after receiving STZ were considered to be diabetic. Body weight and blood glucose were detected every week. All experiments were performed in accordance with regulations specified by the Guide for the Care and Handling of Laboratory Animals (NIH Publication no. 85-23). For the treatments, rats were instilled with 0.5% and 1% COMPOUND I eye drops. Both eyes of all rats were instilled with 1 drop of ophthalmic solution 3 times a day for 6 weeks after diabetes production. Rats were treated with 0.5% and 1% COMPOUND I or vehicle solution eye drops 3 times a day for 4 weeks after glucose levels determination. Animal care and treatment were followed by the institutional guidelines.

After induction of general anesthesia, the right jugular vein and right iliac artery were cannulated with 0.28- and 0.58-mm internal diameter polyethylene tubing, respectively, which were filled with heparinized saline (50 IU heparin/ml saline). Evans blue (Sigma-Aldrich, St. Louis, Md.) was injected through the jugular vein over 10 seconds at a dosage of 45 mg/kg. Immediately after Evans blue infusion, the rats turned visibly blue, confirming their uptake and distribution of the dye. Subsequently, at 15-minute intervals, 0.1 ml blood was drawn from the iliac artery for 2 hours to obtain the time-averaged plasma Evans blue concentration. After the dye had circulated for 120 minutes, the chest cavity was opened, and rats were perfused for 2 minutes via the left ventricle at 37° C. with 0.05 M, pH 3.5, citrate-buffered paraformaldehyde (Sigma-Aldrich, St. Louis, Md.). A pH of 3.5 was used to optimize binding of Evans blue to albumin and the perfusion solution was warmed to 37° C. to prevent vasoconstriction.

Immediately after perfusion, both eyes were enucleated and dissected at the equator. The retinas were carefully dissected away under an operating microscope and thoroughly dried in vacuum equipment for 5 hours. The dry weight was used to normalize the quantitation of Evans blue leakage. Evans blue was extracted by incubating each retina in 150 ml formamide (Sigma-Aldrich. St. Louis. Md.) for 18 hours at 70° C. The supernatant was centrifuged through centrifuge tube with filter at 6000 rpm for 1 hour, and 100 µl of the filtrate was used for triplicate spectrophotometric measurements (SmartSpec, Bio-Rad). Each measurement occurred over a 5-second interval, and all sets of measurements were preceded by known standards. The background-subtracted absorbance was determined by measuring each sample at both 620 nm, the absorbance maximum for Evans blue in formamide, and 740 nm, the absorbance minimum.

The concentration of dye in the extracts was calculated from a standard curve of Evans blue in formamide. BRB breakdown was calculated using the following equation, with results being expressed in inhibition of BRB breakdown (%): [(Concentration in vehicles control group)−(Concentration in non-diabetic or COMPOUND I treated group)]/(Concentration in vehicles control group)×100%.

3.2 Results

Figure 8:
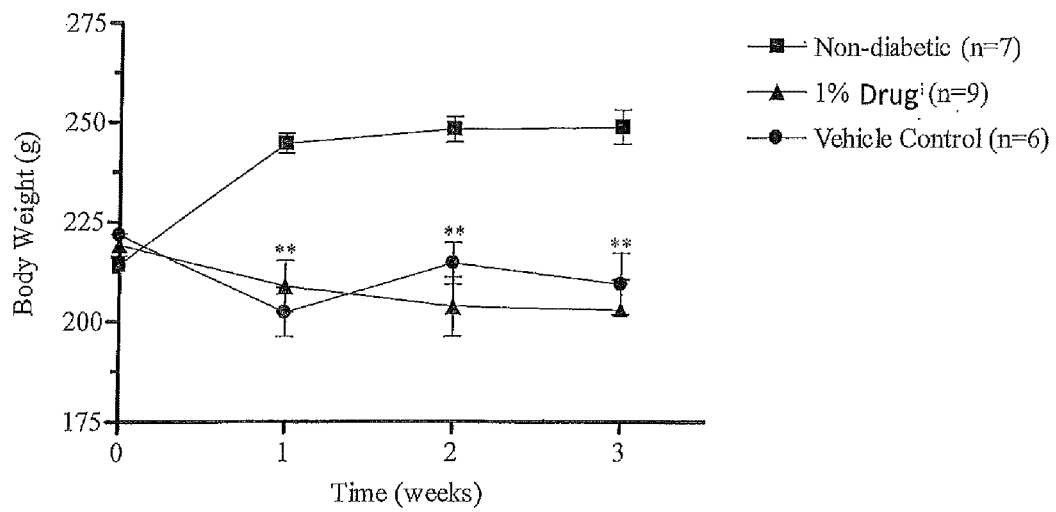
FIG. 8 shows the changes of body weight after streptozotocin injection as compared with normal animals. Data were expressed as means±SEM and **, P<0.01 as compared with control group.
Figure 9:
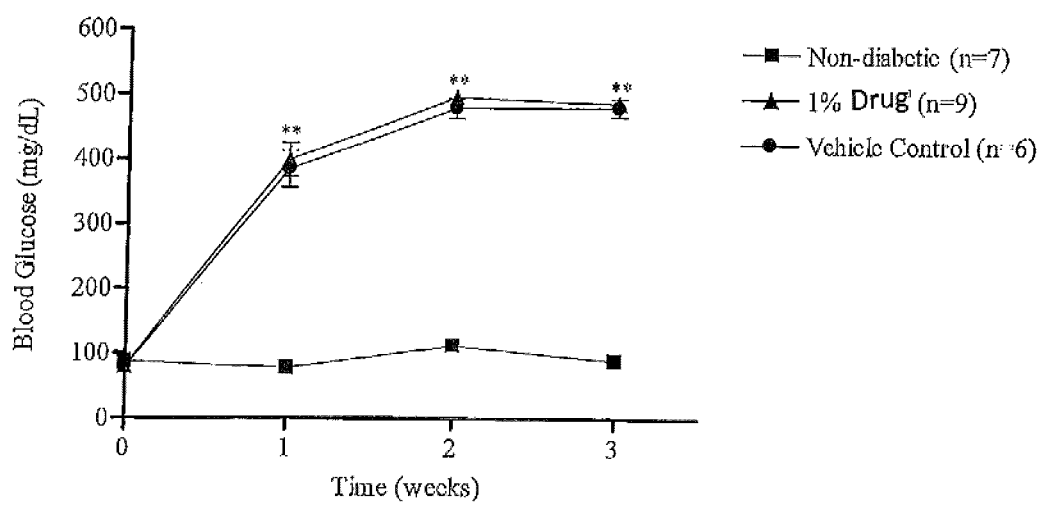
FIG. 9 shows the changes of blood glucose level after streptozotocin injection as compared with normal animals. Data were expressed as mean±SEM and **, P<0.01 as compared with control group.

The body weight of non-diabetic rats increased steadily over 3 week period while the body weight of diabetic rats declined gradually regardless of drug treated or not (FIG. 8). As for blood glucose levels, diabetic rats increased steadily regardless of drug treated or not (FIG. 9). Whereas the blood glucose of non-diabetic remained low at 100 mg %.

Figure 10:
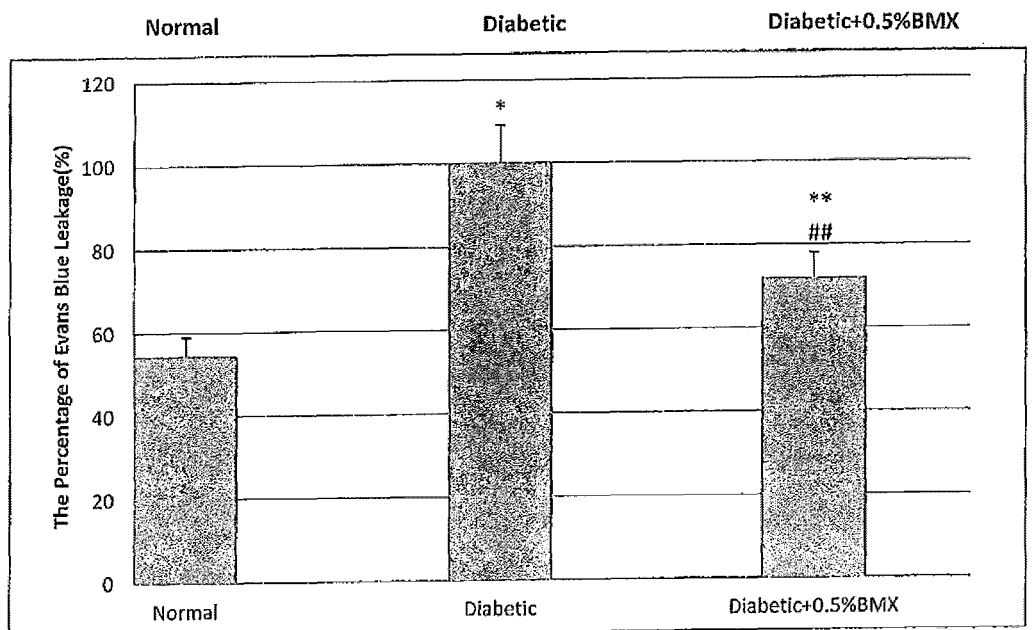
FIG. 10 shows the effects of 0.5% BMX on streptozotocin-induced diabetic edema. 0.5% BMX suppressed the Evans blue leakage of diabetic animals (100%) markedly to 68% (P<0.01), which was closer to the normal animals at 54% level. Data were expressed as mean±SD with n=18 in 0.5% BMX group and n=26 in diabetic group, *, P<0.01 as compared with normal group. **, P<0.01 as compared with DR group and ##, P<0.01 as compared with normal group.
Figure 11:
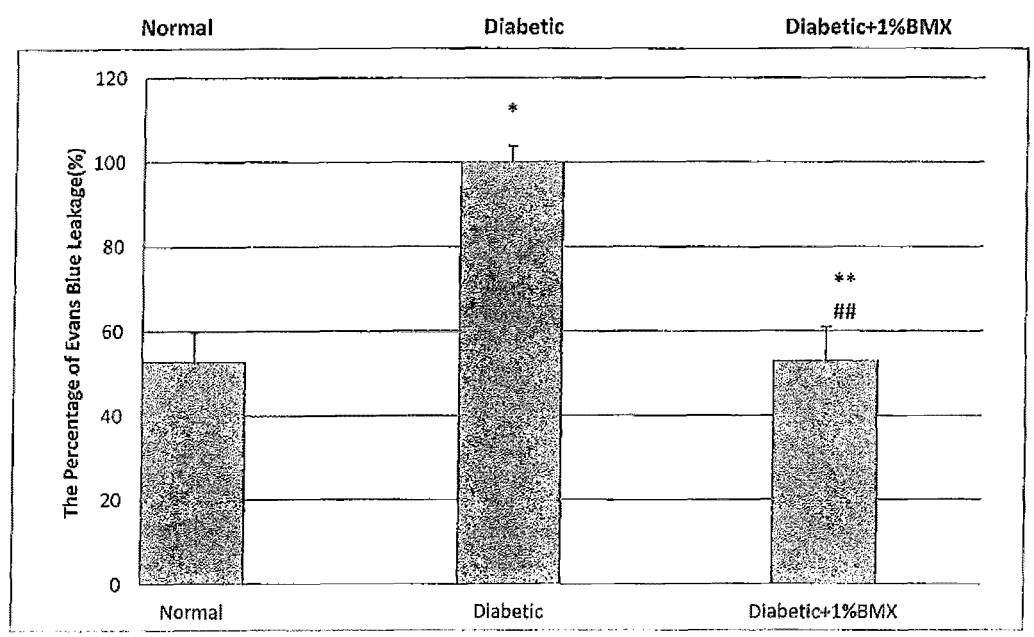
FIG. 11 shows the effects of 1.0% BMX on streptozotocin-induced diabetic macular edema. BMX suppressed the Evans blue leakage of diabetic animals markedly in a dose-response relationship. 1% BMX suppressed the Evans blue leakage (56%) completely to the level of normal animals (56%). Data were expressed as mean±SD with n=16 in 1% BMX group and n=26 in diabetic group. *, P<0.01 as compared with normal group, **, P<0.01 as compared with diabetic animals and ##, P>0.05 as compared with normal control animals.

The percentage of Evans blue leakage in normal non-diabetic group and 0.5% COMPOUND I and 1% COMPOUND I treated group were 54%, 68% and 56% compared with diabetic vehicle control group as 100%, respectively (FIG. 10 and FIG. 11). There was significant difference between diabetic vehicle control group and all the other groups (FIG. 10 and FIG. 11). However, there was no difference between non-diabetic control group and 1% COMPOUND I treated group (FIG. 10 and FIG. 11).

These results indicate that the Evans Blue leakage of DME can be blocked completely by 1% COMPOUND I and partially by 0.5% COMPOUND I, showing a good dose response relationship (FIG. 10 and FIG. 11).

The BRB breakdown causes vascular permeability or vascular leakage which is an early complication of diabetes and major cause of DME. The BRB has two components: the outer and the inner barriers. The outer barrier is formed by tight junctions between retinal pigment epithelium (RPE) cells and includes zonula occludens and desmosomes. The inner barrier is formed by tight junctional complexes between retinal vascular endothelial cells and a well-differentiated network of glial cells (astrocytes and Miller cells). Several clinical studies suggest that the inner barrier is the primary site of vascular leakage that results in DME. The mechanism of the BRB breakdown is multifactorial and secondary to changes in the tight junctions, pericyte and endothelial cell loss, retinal vessel dilation and leukostasis and vitreo-retinal taut and traction. The retinal vessel tight junctions protect the vessels from leaking, but sustained hyperglycemia could damage tight junctions and the vessels could become leaky, allowing fluid or blood to seep into the retina, thus resulting in retinal swelling. The BRB integrity was analyzed by Evans blue leakage method, 6 weeks after diabetes induction. Evans blue leakage of diabetic animals was much higher than non-diabetic animals, demonstrating significant difference between the diabetic group and non-diabetic group (FIG. 10 and FIG. 11). In the experiments done in our laboratory before, Osthole showed efficacy to reduce vascular permeability in experimentally-induced ocular inflammation and to inhibit IL-1-induced uveitis in rat eyes. Our study indicated that BMX significantly reduced vascular permeability in the STZ-induced diabetic animal model. Moreover, 1% BMX completely restored diabetic BRB breakdown to non-diabetic levels (FIG. 11).

Example 4: Effects of Compound I on Streptozotocin-Induced Diabetic Retinopathy

Glial fibrillary acidic protein (GFAP) is an established indicator of retinal stress. In the normal mammalian retina, GFAP is marginally detectable in Müller cells. When under stress, activated Müller cells express high levels of GFAP. In the present research, increased GFAP expression was demonstrated in Miller cells, indicating that Miller cell dysfunction was involved in STZ-induced diabetic retinopathy, which is consistent with previous studies. Müller cell dysfunction leads to glutamate transport abnormality, which is toxic to neuronal cells. Neuronal dysfunction or cell loss in diabetic retinas might partly be due to Müller cell dysfunction.

Vision loss and blindness from diabetic retinopathy are usually the results of vascular leakage or ischemia. Vascular leakage involves hemorrhage or the formation of hard exudates. Ischemia from vascular damage and disruption in local perfusion results in angiogenesis and neovascularization. The new blood vessels formed are fragile and prone to hemorrhage, which can impair vision, ultimately causing blindness. VEGF is major regulation of blood vessel formation and function. It controls several processes in endothelial cells, such as proliferation, survival, and migration. Retinal VEGF expression is correlated with diabetic blood-retinal barrier breakdown and ischemia related neovascularization in animals and humans. In the present study, VEGF expression in Miller cells was significantly upregulated in diabetic retina, indicating that VEGF overexpression plays a crucial role in retinal vascular abnormality in STZ-induced diabetes. In this study, we tried to investigate whether GFAP and VEGF up-regulation by diabetes could be suppressed by COMPOUND I.

4.1 Methods 4.1.1 Animals

After a 16-hour fasting, Sprague-Dawley female rats weighing 200-220 g received a single 60 mg/kg intraperitoneal injection of Streptozotocin (STZ; Sigma-Aldrich, St. Louis, Md.) in 10 mM sodium citrate buffer (pH 4.5; Sigma-Aldrich, St. Louis, Md.). Control rats were fasted and received the buffer solution alone. Rats with blood glucose levels higher than 375 mg/dL 7 days after receiving STZ were considered to be diabetic. Diabetic rats were treated with 1% COMPOUND I, 0.5% COMPOUND I or vehicle eye drops 3 time a day for 6 weeks.

4.1.2 Western Blot Assays

After rats were sacrificed as described in last section, eyes were enucleated and bisected. Retinas were peeled from eyecups and immediately homogenized with 0.3 ml ice-cold lysis buffer (STZ; Sigma-Aldrich, St. Louis, Mo.), including 1 µl proteinase inhibitor cocktail (STZ; Sigma-Aldrich, St.

Louis, Mo.). The insoluble material was removed by centrifugation at 12,000 g for 20 minutes. Final protein concentrations were determined using a protein assay kit (BCA, Santa Cruz Biotechnology, Santa Cruz, Calif.) according to manufacturer's specifications. The homogenate (80 µg) were separated by NuPAGE Bis-Tris Mini Gels (Invitrogen Life Technologies, Grand Island, N.Y.) and transferred to nitrocellulose membranes by iBlot Gel transfer Device (Invitrogen Life Technologies, Grand Island, N.Y.). The nitrocellulose membranes were treated by BenchPro 4100 Card Processing Station (Invitrogen Life Technologies, Grand Island, N.Y.) according to the instruction of Western-Breeze® Chromogenic Kit-Anti-Rabbit (Invitrogen Life Technologies, Grand Island, N.Y.). The primary antibodies used were anti-GFAP (1:200, Santa Cruz Biotechnology, Santa Cruz, Calif.) and glycealdehyde-3-phosphate dehydrogenase (GAPDH) (1:100), respectively. The Anti-rabbit IgG, AP-linked antibody was used as a second antibody. For quantitative evaluation of the western blot studies, the nitrocellulose membranes were scanned and the optical densities were quantified with analysis software (Pro-gel Analyzer software, Media Cybernetics, Rockville, Md.).

4.1. 3 Quantitative Real-Time PCR

After rat were sacrificed as described previously, the eyes were enucleated and bisected, and the retinas were peeled from the eyecups and immediately homogenized in RNA isolation agent (RNeasy®Plus Mini Kit, Qiagen, Valencia, Calif.). The first-strand cDNA was prepared from the mRNA by using the commercial kit in accordance with the manufacturer's protocol (High-capacity reverse transcription kits, AB life technologies, Austin, Tex.). The sequences of primers were listed in Table 1. Real-time PCR was performed in 96-well plates using standard protocols with a fluorescent detection dye (SYBRR Green PCR Master Mix, AB life technologies, Austin, Tex.) in a real-time detection system (iCycler. Bio-Rad). All PCR reactions were a final volume of 20 µl comprised of fluorescent dye/PCR mix, final concentration 0.2 µM forward and reverse primers, and 1 ng of cDNA. The PCR cycle parameters were as follows: polymerase activation for 15 minutes at 90° C., 40 cycles of 95° C. for 15 seconds, 60° C. for 30 seconds and 72° C. for 1 minute. The quantity of mRNA was calculated by normalizing the CT of the β-actin housekeeping gene in the same sample, according to the following formula: The average β-actin CT (each multiplex PCR was performed in triplicate) was subtracted from the average target gene CT; the results represented the ΔCT. This ΔCT is specific and can be compared with the ΔCT of a calibration sample. The subtraction of control ΔCT from the ΔCT of the target gene is referred ΔΔCT. The relative quantification of expression of a target gene (in comparison with control) was determined by using $2^{-\Delta\Delta CT}$.

| Table Sequences of oligonucleotides used as primers. | | |
|---|---|---|
| Target gene | | Sequence (5'-3') |
| GFAP | Sense | CCGTTCTCTGGAAGACACTGAAAC |
|  | Antisense | TTGGAAGGATGGTTGTGGATTC |
| β-Actin | Sense | AGGCCAACGGTGAAAAGATG |
|  | Antisense | ACCAGAGGCATACAGGGACAA |

4.1.4 Statistical Analysis

All data were expressed as means±SD. Normally distributed data in two groups were analyzed with a Student's t-test. For pairwise comparisons, a Paired t-test was used between two groups. A value of P<0.05 was considered statistically significant.

4.2 Results 4.2.1 Western Blot Assays 7 weeks after intraperitoneal injection of STZ, the protein expression of GFAP in retina of diabetic control group were significantly increased as compared with non-diabetic group (P<0.05). The expression of GFAP proteins in retina was significantly suppressed as compared with diabetic control group (P<0.05, FIG. 12 and FIG. 13) after diabetic rats were instilled with 1% COMPOUND I and 0.5% COMPOUND I tid. for 6 weeks.

Figure 12:
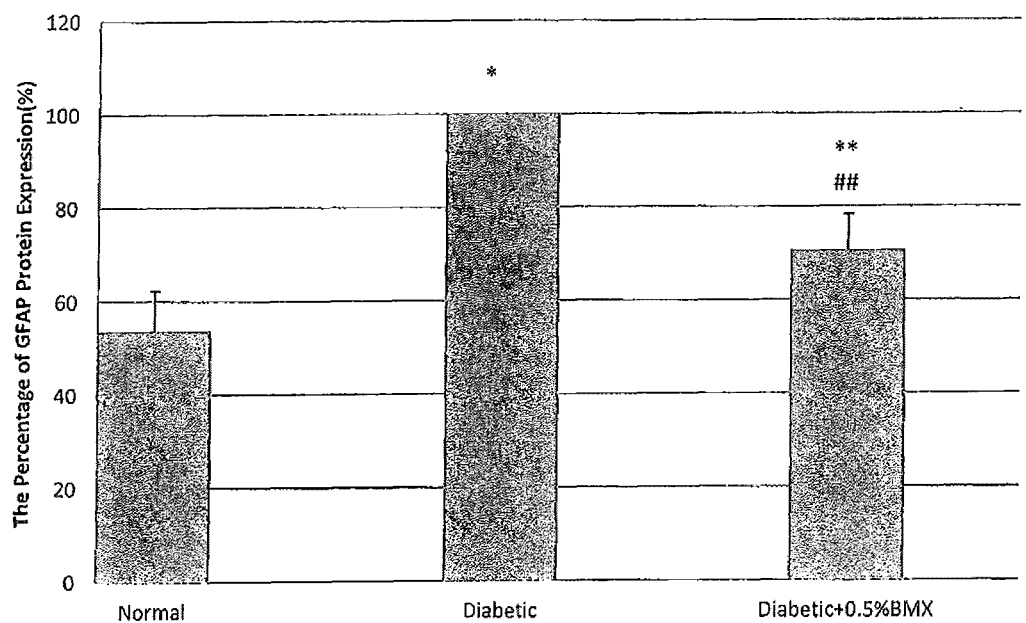
FIG. 12 shows the effects of 0.5% BMX on GFAP levels in streptozotocin-induced diabetic retinopathy (DR) with Western Blot experiments, indicating that GFAP up-regulation in DR by 0.5% BMX is in a dose related manner. The up-regulation of GFAP in DR animals (as 100%) was markedly suppressed by 0.5% BMX to 70% level and was closer to the GFAP levels in normal animals at 53% of DR animals. Data were expressed as mean±SD with n=6 in all groups. *, p<0.01 as compared with normal group, **, P<0.01 as compared with DR group and ##, P<0.01 as compared with normal group.
Figure 13:
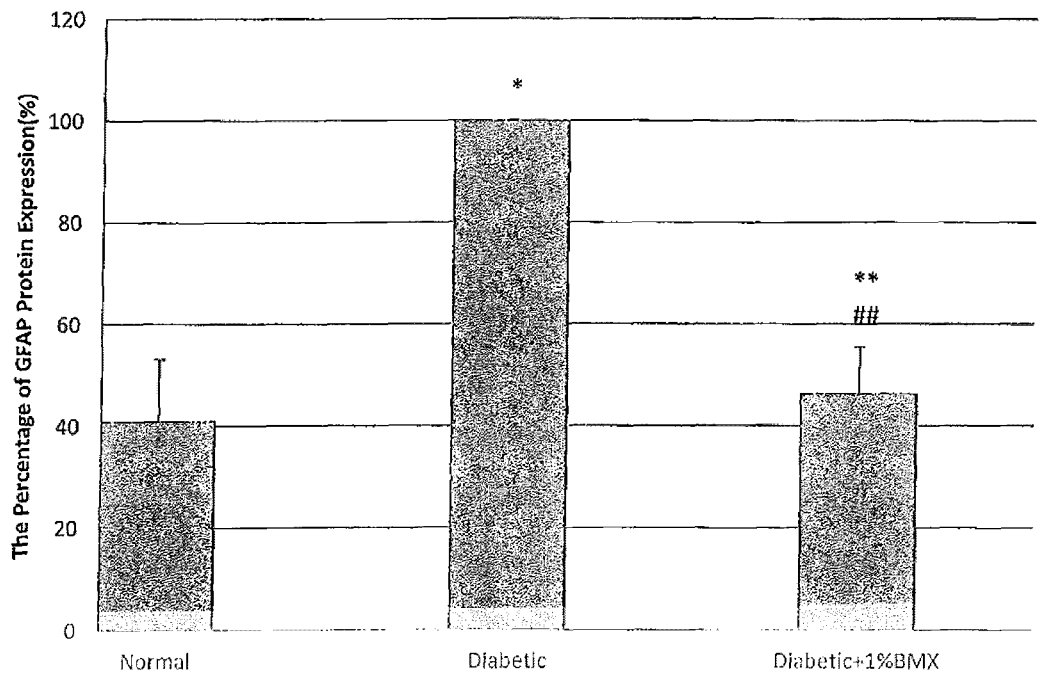
FIG. 13 shows the effects of 1.0% BMX on GFAP levels in streptozotocin-induced diabetic retinopathy (DR) with Western Blot experiments, indicating that GFAP up-regulation in DR by 1.0% BMX is in a dose related manner. The up-regulation of GFAP in DR rats (as 100%) was markedly suppressed by 1.0% BMX to 46% level and was very close to that of normal rats at 41%. Data were expressed in mean±SD with n=5 in all groups. *, p<0.01 as compared with normal group, **, P<0.01 as compared with diabetic group and ##, P>0.05 as compared with normal group animals.

These results clearly indicated that diabetic retinopathy can be treated by COMPOUND I in a dose-dependent manner (FIG. 12 and FIG. 13).

Figure 14:
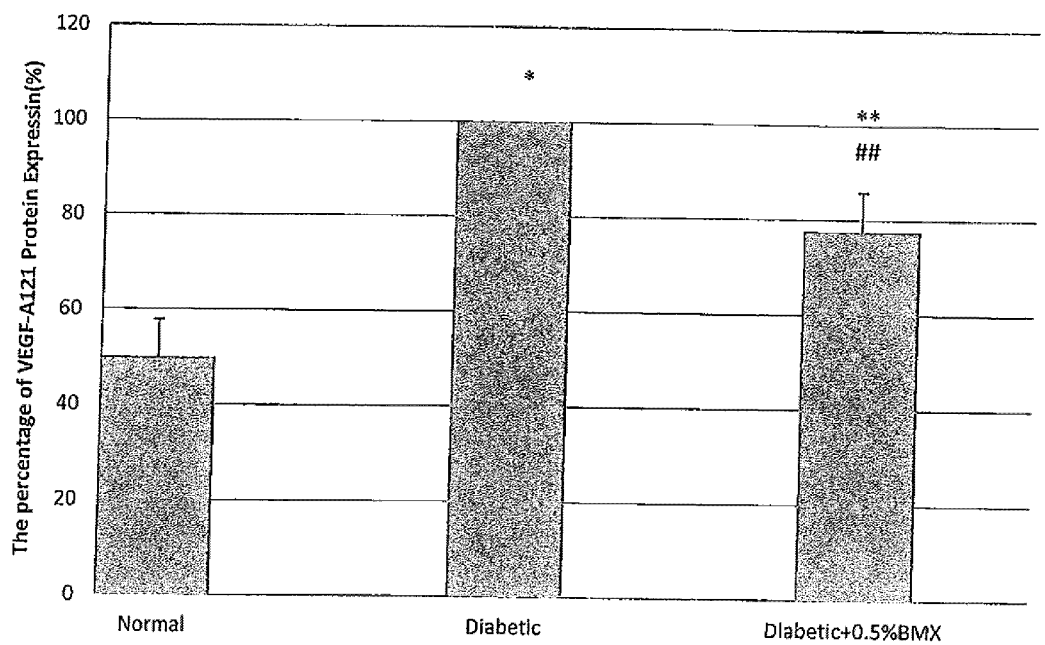
FIG. 14 shows the effects of 0.5% BMX on VEGF levels in streptozotocin-induced diabetic retinopathy (DR) with Western Blot experiments, indicating that VEGF up-regulation in DR by 0.5% BMX is in a dose related manner. The up-regulation of VEGF in DR animals (as 100%) markedly suppressed by 0.5% BMX to 77% level and was closer to the VEGF levels in normal animals at 50% of DR animals. Data were expressed as mean±SD with n=6 in all groups. *, p<0.01 as compared with normal group, **, P<0.01 as compared with DR group and ##, P<0.01 as compared with normal group.
Figure 15:
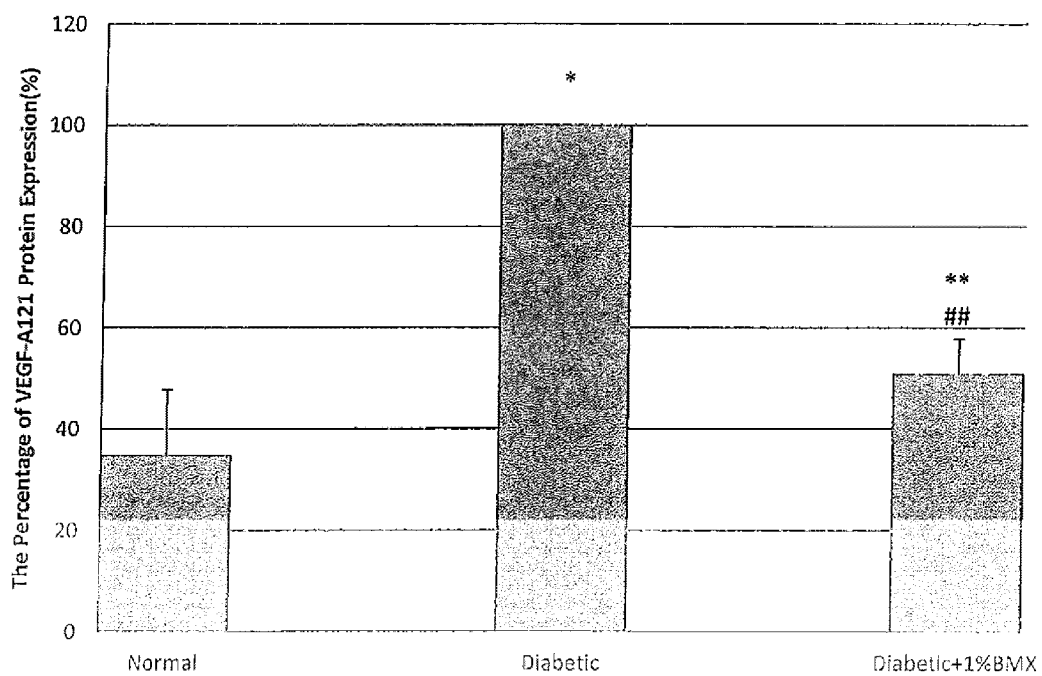
FIG. 15 shows the effects of 1.0% BMX on VEGF levels in streptozotocin-induced diabetic retinopathy (DR) with Western Blot experiments, indicating that VEGF up-regulation in DR by 1.0% BMX is in a dose related manner. The up-regulation of VEGF in DR rats (as 100%) was markedly suppressed by 1.0% BMX to 50% level and was very close to that of normal rats at 34%. Data were expressed in mean±SD with n=3 in all groups. *, p<0.01 as compared with normal group, **, P<0.01 as compared with diabetic group and ##, P<0.05 as compared with normal group animals.

VEGF is another biomarker increased markedly in diabetic retinopathy as can be seen a significant increase of VEGF in diabetic eyes as compared with the control normal eyes (FIG. 14 and FIG. 15). The VEGF level in diabetic eyes was markedly suppressed by 0.5% COMPOUND I and 1% COMPOUND I (FIG. 14 and FIG. 15), indicating that the diabetic retinopathy can be treated effectively in a dose dependent matter (FIG. 14 and FIG. 15).

4.2.2 Quantitative Real-Time PCR

Figure 16:
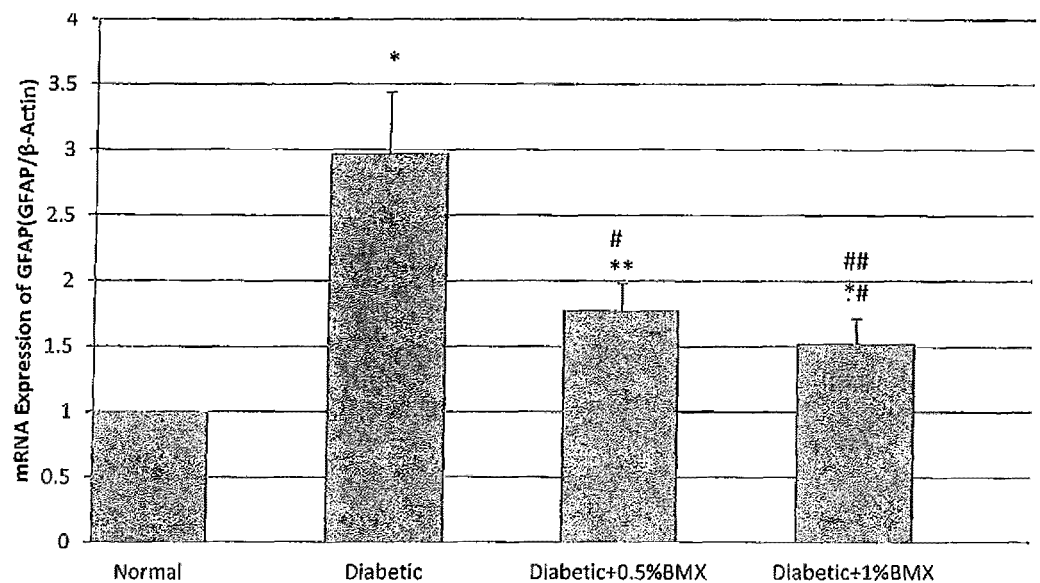
FIG. 16 shows the effects of BMX on the gene expression of GFAP in streptozotocin induced diabetic retinopathy (DR) with PCR analysis. The mRNA expression of GFAP was markedly increased to 3.0 folds of normal control level in DR animals (as 100%), which was suppressed by 0.5% BMX and 1% BMX to 60% and 51%, respectively. The GFAP of normal animals was 34% of DR rats. These results indicate that BMX can suppress mRNA expression of GFAP in DR significantly in a dose-response manner. Data were expressed in mean±SD with n=9 in normal group, n=9 in diabetic group, n=7 in 0.5% BMX group and n=5 in 1% BMX group. *, p<0.01 as compared with normal group, #, P<0.05 and ##, P<0.01 as compared with DR animal and **, P<0.01 and *#, P<0.05 as compared with normal group.

The gene expression of GFAP was detected by quantitative real-time PCR. The results indicated that non-diabetic retinas expressed low levels GFAP (FIG. 16). Six weeks after onset of diabetes, the gene expression of GFAP was significantly up-regulated. The GFAP expression was significantly down-regulated by treatment with 0.5% and 1% COMPOUND I as compared with diabetic control group (FIG. 16).

These results were similar to those obtained with Western Blot which was presented in the previous section (FIG. 12 and FIG. 13). The markedly up-regulated GFAP expression was significantly suppressed by 0.5% COMPOUND I and 1% COMPOUND I in a dose dependent manner and was closer to the control level (FIG. 16).

These results clearly indicate that COMPOUND I could be used for the treatment of diabetic retinopathy.

Example 5: In Vivo Efficacy of Compound I (BMX) in a Mouse Model of CNV 5.1 Materials and Methods 5.1.1 Animals Male C57BL/6J mice (BioLASCO Taiwan Co.) were maintained within the Animal Center at Taipei Medical University (TMU) and the CNV study was performed in accordance with ARVO statement and the experimental protocols were approved by the Institutional Animal Care and Use Committee of TMU (LAC-2017-0130). To create CNV, mice were anesthetized by injection of Balanzine (10% xylazine) (10 mg/kg) and Ketamine (80 mg/kg). The rupture of Bruch's membrane-choroid was achieved by laser photocoagulation (Micron III system, Phoenix Research Laboratories, Pleasanton, Calif.) using CNV laser burns of four spots (0.1-second duration, 250 mW) approximately two disc-diameters away from the optic disc. Mice were randomly allocated into three groups: (1) mice received treatment with vehicle only; (2) mice received CVN laser burn and treatment with vehicle only; (3) mice received CNV laser burn and treatment with 25 mg/kg/d for 7 or 28 days of BMX delivered systemically through oral administration. On day −7, 7 and 28, Fundus photography (FP) and fundus fluorescein angiography (FFA) were carried out on mice under anesthesia to obtain retinal angiography data immediately after intraperitoneal injection of sodium fluorescein as described below.

5.1.2 Fundus Photography (FP) and Fundus Fluorescein Angiography (FFA)

A Micron III retinal imaging microscope (Phoenix Research Laboratories, Pleasanton, Calif.) was used to monitor morphological and pathological changes in the fundus of C57BL/6 mice. Briefly, mice were anesthetized by IP injection of ketamine (80 mg/kg) and xylazine (10 mg/kg), and eyes were dilated with 0.125% atropine. Each mouse was held on its side on the microscope platform and the right eye was rinsed with 2% Methocel gel (OmniVision, SA, Neuhausen, Switzerland). After color FP was performed, fluorescein (10%; 0.05 mL) was used for FFA examination through IP injection. Serial images were then collected using SteamPix 5™ software.

5.1.3 Optical Coherence Tomography (OCT) Imaging and Thickness Analysis

The OCT module of the Micron III (Phoenix Research Laboratories, Pleasanton, Calif.) retinal imaging microscope was used to obtain images from retinal layers. A high-resolution b-scan of retinal cross-sections (right eye) was obtained by averaging and spatially aligning 5 individual b-scans along the same vertical axis. Retinal layers were segmented using InSight XL (Phoenix Research Laboratories, San Ramon, Calif., SA) for further analysis. Three retinal layers were defined and measured in the C57BL/6 mice included in this study: the inner layer, which comprises the retinal nerve fiber layer (RNFL), the ganglion cell layer (GCL), and the inner plexiform layer (IPL); the middle layer, which comprises the inner nuclear layer (INL), the outer plexiform layer (OPL), the outer nuclear layer (ONL), and the outer limiting membrane (OLM); and the outer layer, which comprises the inner and outer segments (IS/OS) of the photoreceptors and the retinal pigment epithelium.

5.2 Results

Figure 17A:
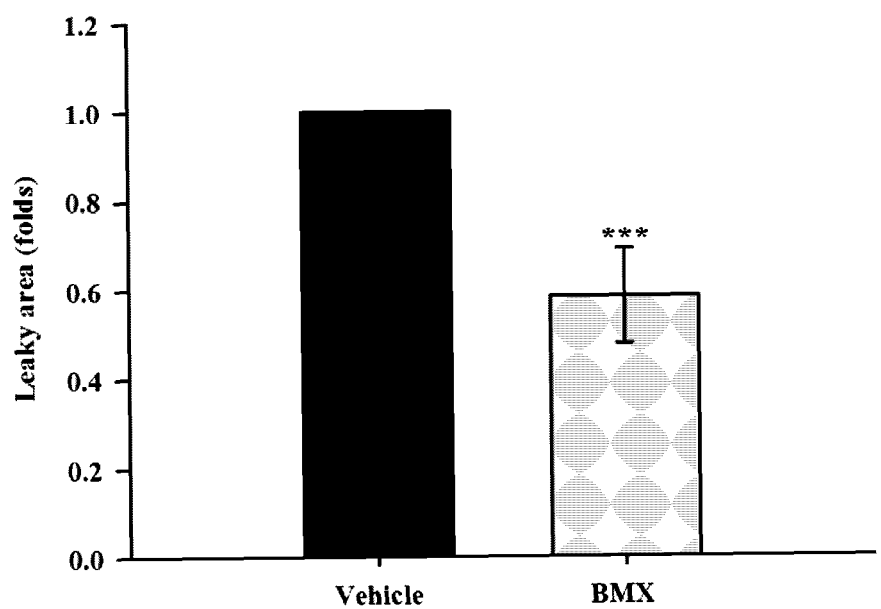
FIG. 17A shows the comparison of leaky areas between vehicle group and BMX group.
Figure 17B:
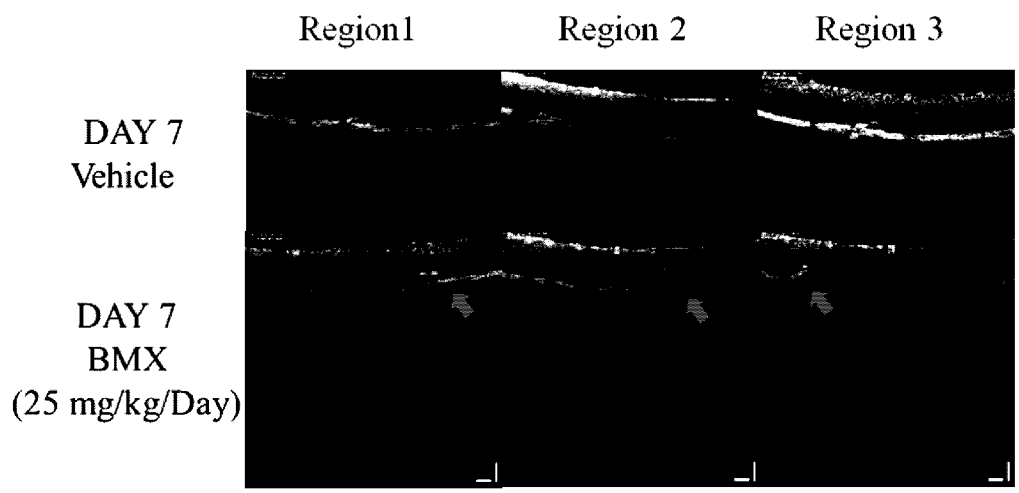
FIG. 17B shows the optical coherence tomography (OCT) images of mouse retina on day 7. Arrow: laser damage area.
Figure 18A:
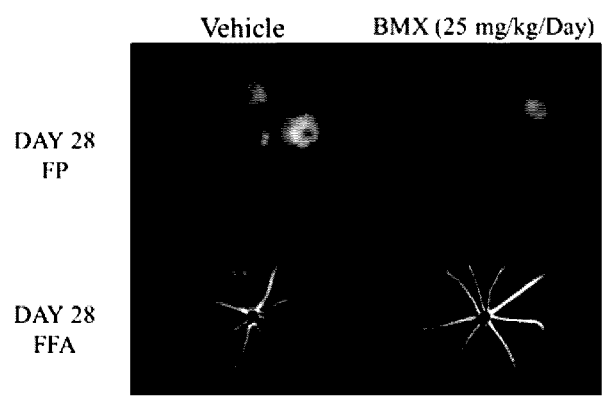
FIG. 18A shows the fundus photography (FP) and fundus fluorescein angiography (FFA) images of mice on day 28.
Figure 18B:
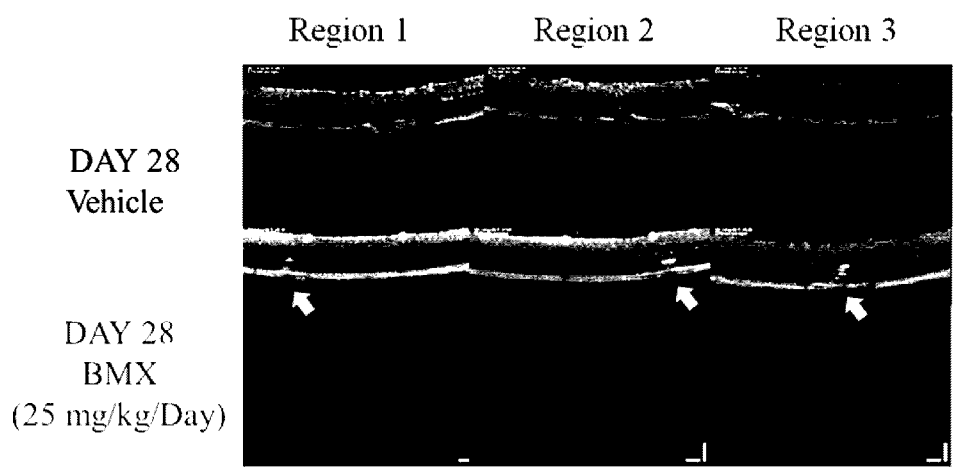
FIG. 18B shows the OCT images of mouse retina on day 28. Arrow: laser damage area.

The results are shown in FIGS. 17A-18B. The leaky area in the BMX group was significantly reduced (FIGS. 17A and 18A). Further, according to the FP and FFA images, tissue hyperplasia resulted from laser damage was ameliorated in the BMX group (FIGS. 17B (day 7) and 18B (day 28)).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for treating an ocular disease through reversing injury of retinal pigment epithelium (RPE) cells and enhancing ocular blood flow, comprising administering to a subject in need thereof an effective amount of a compound having the structure of Formula A1:

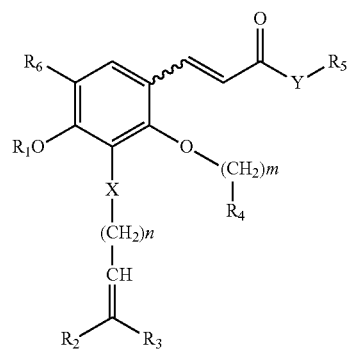

wherein $R^1$ is hydrogen, alkyl, alkenyl, $C_5$-$C_6$ cycloalkyl, 5-membered or 6-membered unsaturated carbocycle or 5-membered or 6-membered heterocycle; $(CH_2)m$ $R^4$ X is C, —O—, —N— or —S—;

Y is —O—, —NH or —O—$C_1$-$C_4$ alkyl;

n is an integer of 0 to 10;

m is an integer of 0 to 5;

$R^2$ and $R^3$ is independently $C_1$-$C_6$ alkyl;

$R^4$ is $C_5$-$C_6$ cycloalkyl or 5-membered or 6-membered unsaturated carbocycle or heterocycle which may be substituted with halogen, —$CF_3$, —$OR^7$ or —$NR^7R^8$, wherein $R^7$ and $R^8$ are independently hydrogen or $C_1$-$C_6$ alkyl;

$R^5$ is OH, $NH_2$ or $C_5$-$C_6$ cycloalkyl, 5-membered or 6-membered unsaturated carbocycle or heterocycle wherein the cycloalkyl, carbocycle and heterocycle may be optionally substituted with halogen, $NH_2$, $NO_2$, $C_1$-$C_6$ alkoxy, $C_{1-6}$ alkylthio, $OR^{7''}$, $NR^7R^8$ or $CF_3$; and $R^6$ is H, $C_1$-$C_{10}$ alkyl which may be substituted by hydroxy or $C_2$-$C_{10}$ alkenyl, or together with $R_1$ being —$C_2H_2$—, or a pharmaceutically acceptable salt, stereoisomer, enantiomer, prodrug or solvate thereof, wherein the ocular disease is selected from the group consisting of proliferative vitreoretinopathy (PVR), uveitis, early stage of age-related macular degeneration (AMD), diabetic retinopathy (DR), and diabetic macular edema (DME).

2. The method of claim 1, wherein the compound is formulated into eye ointment, eye gel, eye cream, or eye drops.

3. The method of claim 1, wherein the compound is topically administered.

4. The method of claim 1, wherein the compound is:

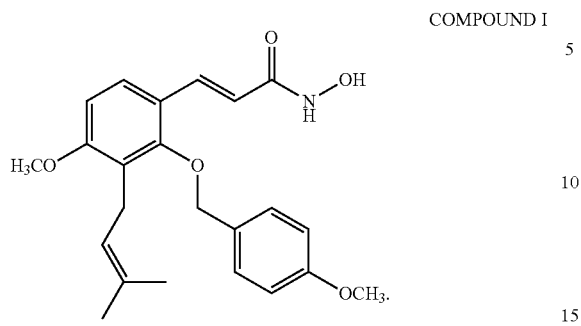

COMPOUND I

5. The method of claim 1, wherein the compound of general Formula A1 is administered orally to the subject 1-3 times a day and wherein an amount of the compound of general Formula A1 is from 0.5 to 50 mg in each oral administration.

6. The method of claim 4, wherein the compound I is administered orally to the subject 1-3 times a day and wherein an amount of the compound I is from 0.5 to 50 mg in each oral administration.

* * * * *